(12) United States Patent
DeSantis et al.

(10) Patent No.: US 9,005,238 B2
(45) Date of Patent: Apr. 14, 2015

(54) ENDOSCOPIC SURGICAL DEVICES

(75) Inventors: Robert DeSantis, Redding, CT (US); Thomas Wingardner, North Haven, CT (US); Anthony Ceniccola, Branford, CT (US)

(73) Assignee: Covidien LP, Mansfield, MA (US)

( * ) Notice: Subject to any disclaimer, the term of this patent is extended or adjusted under 35 U.S.C. 154(b) by 1882 days.

(21) Appl. No.: 12/193,864

(22) Filed: Aug. 19, 2008

(65) Prior Publication Data
US 2009/0054734 A1 Feb. 26, 2009

Related U.S. Application Data

(60) Provisional application No. 60/965,857, filed on Aug. 23, 2007.

(51) Int. Cl.
*A61B 17/00* (2006.01)
*A61B 1/008* (2006.01)
*A61B 17/29* (2006.01)

(52) U.S. Cl.
CPC ............. *A61B 1/008* (2013.01); *A61B 17/2909* (2013.01); *A61B 2017/003* (2013.01); *A61B 2017/00424* (2013.01); *A61B 2017/2905* (2013.01); *A61B 2017/291* (2013.01); *A61B 2017/292* (2013.01)

(58) Field of Classification Search
CPC ...................... A61B 17/2909; A61B 2017/291; A61B 2017/2918–2017/2922; A61B 1/00066; A61B 1/0008; A61B 1/00098; A61B 2017/003; A61B 2017/00318; A61B 2017/00424; A61B 2017/2905
USPC .................................. 606/205; 600/146, 149
See application file for complete search history.

(56) References Cited

U.S. PATENT DOCUMENTS

| | | | |
|---|---|---|---|
| 2,028,635 A | 1/1936 | Wappler | |
| 2,507,710 A | 5/1950 | Grosso | |

(Continued)

FOREIGN PATENT DOCUMENTS

| | | | |
|---|---|---|---|
| EP | 0095970 A2 | 12/1983 | |
| EP | 0448284 A2 | 9/1991 | |

(Continued)

OTHER PUBLICATIONS

European Search Report for EP 08 252797.9-2319 date of completion is Nov. 7, 2008 (6 pages).

(Continued)

*Primary Examiner* — Katherine Dowe

(57) ABSTRACT

According to an aspect of the present disclosure, an endoscopic surgical device is provided and includes a handle assembly; a tube assembly operatively supported on and extending from the handle assembly, the tube assembly defining a longitudinal axis; an articulation assembly operatively supported on and extending from a distal end of the tube assembly; and a tool assembly operatively supported on and extending from a distal end of the articulation assembly. In use, a rotation of the handle assembly about the longitudinal axis results in a concomitant rotation of the tool assembly; an actuation of the handle assembly in a particular manner results in a concomitant actuation of the tool assembly; and a pivoting of the handle assembly in any off-axis direction relative to the longitudinal axis results in a concomitant articulation of the tool assembly via the articulation assembly.

28 Claims, 32 Drawing Sheets

(56) References Cited

U.S. PATENT DOCUMENTS

| | | |
|---|---|---|
| 2,790,437 A | 4/1957 | Moore |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,669,471 A | 6/1987 | Hayashi |
| 4,688,554 A | 8/1987 | Habib |
| 4,728,020 A | 3/1988 | Green et al. |
| 4,763,669 A | 8/1988 | Jaeger |
| 4,872,456 A | 10/1989 | Hasson |
| 4,880,015 A | 11/1989 | Nieman |
| 4,944,093 A | 7/1990 | Falk |
| 4,944,741 A | 7/1990 | Hasson |
| 4,945,920 A | 8/1990 | Clossick |
| 4,950,273 A | 8/1990 | Briggs |
| 4,982,727 A | 1/1991 | Sato |
| 5,002,543 A | 3/1991 | Bradshaw et al. |
| 5,035,248 A | 7/1991 | Zinnecker |
| 5,042,707 A | 8/1991 | Taheri |
| 5,080,663 A | 1/1992 | Mills et al. |
| 5,100,430 A | 3/1992 | Avellanet et al. |
| 5,133,727 A | 7/1992 | Bales et al. |
| 5,137,013 A | 8/1992 | Chiba et al. |
| 5,152,779 A | 10/1992 | Sanagi |
| 5,209,747 A | 5/1993 | Knoepfler |
| 5,228,451 A | 7/1993 | Bales et al. |
| 5,238,002 A | 8/1993 | Devlin et al. |
| 5,254,130 A | 10/1993 | Poncet et al. |
| 5,271,381 A | 12/1993 | Ailinger et al. |
| 5,273,026 A | 12/1993 | Wilk |
| 5,275,608 A | 1/1994 | Forman et al. |
| 5,308,353 A | 5/1994 | Beurrier |
| 5,314,424 A | 5/1994 | Nicholas |
| 5,318,528 A | 6/1994 | Heaven et al. |
| 5,330,502 A | 7/1994 | Hassler et al. |
| 5,336,221 A | 8/1994 | Anderson |
| 5,344,428 A | 9/1994 | Griffiths |
| 5,354,311 A | 10/1994 | Kambin et al. |
| 5,383,880 A | 1/1995 | Hooven |
| 5,383,888 A | 1/1995 | Zvenyatsky et al. |
| 5,383,895 A | 1/1995 | Holmes et al. |
| 5,386,818 A | 2/1995 | Schneebaum et al. |
| 5,395,367 A | 3/1995 | Wilk |
| 5,403,342 A | 4/1995 | Tovey et al. |
| 5,405,344 A | 4/1995 | Williamson et al. |
| 5,411,481 A | 5/1995 | Allen et al. |
| 5,417,203 A | 5/1995 | Tovey et al. |
| 5,419,339 A | 5/1995 | Palmer |
| 5,433,721 A | 7/1995 | Hooven et al. |
| 5,439,467 A | 8/1995 | Benderev et al. |
| 5,441,494 A | 8/1995 | Ortiz |
| 5,454,378 A | 10/1995 | Palmer et al. |
| 5,454,827 A | 10/1995 | Aust et al. |
| 5,474,571 A | 12/1995 | Lang |
| 5,480,406 A | 1/1996 | Nolan et al. |
| 5,490,861 A | 2/1996 | Kratsch et al. |
| 5,501,654 A | 3/1996 | Failla et al. |
| 5,511,564 A | 4/1996 | Wilk |
| 5,514,157 A | 5/1996 | Nicholas et al. |
| 5,520,678 A | 5/1996 | Heckele et al. |
| 5,527,322 A | 6/1996 | Klein et al. |
| 5,535,754 A | 7/1996 | Doherty |
| 5,545,148 A | 8/1996 | Wurster |
| 5,549,617 A | 8/1996 | Green et al. |
| 5,562,686 A | 10/1996 | Sauer et al. |
| 5,569,269 A | 10/1996 | Hart et al. |
| 5,569,299 A | 10/1996 | Dill et al. |
| 5,571,136 A | 11/1996 | Weaver |
| 5,578,056 A | 11/1996 | Pauldrach |
| 5,582,617 A | 12/1996 | Klieman et al. |
| 5,591,202 A | 1/1997 | Slater et al. |
| 5,601,599 A | 2/1997 | Nunez |
| 5,607,450 A | 3/1997 | Zvenyatsky et al. |
| 5,618,294 A | 4/1997 | Aust et al. |
| 5,643,294 A | 7/1997 | Tovey et al. |
| 5,674,230 A | 10/1997 | Tovey et al. |
| 5,702,408 A | 12/1997 | Wales et al. |
| 5,728,107 A | 3/1998 | Zlock et al. |
| 5,728,113 A | 3/1998 | Sherts |
| 5,759,151 A | 6/1998 | Sturges |
| 5,766,196 A | 6/1998 | Griffiths |
| 5,772,578 A | 6/1998 | Heimberger et al. |
| 5,792,152 A | 8/1998 | Klein et al. |
| 5,823,066 A | 10/1998 | Huitema et al. |
| 5,827,177 A | 10/1998 | Oneda et al. |
| 5,830,220 A | 11/1998 | Wan et al. |
| 5,851,208 A | 12/1998 | Trott |
| 5,855,569 A | 1/1999 | Komi |
| 5,871,488 A | 2/1999 | Tovey et al. |
| 5,873,817 A | 2/1999 | Kokish et al. |
| 5,899,425 A | 5/1999 | Corey, Jr. et al. |
| 5,899,914 A | 5/1999 | Zirps et al. |
| 5,904,647 A | 5/1999 | Ouchi |
| 5,908,428 A | 6/1999 | Scirica et al. |
| 5,916,146 A | 6/1999 | Allotta et al. |
| 5,916,147 A | 6/1999 | Boury |
| 5,919,199 A | 7/1999 | Mers Kelly et al. |
| 5,921,956 A | 7/1999 | Grinberg et al. |
| 5,938,678 A | 8/1999 | Zirps et al. |
| 5,944,713 A | 8/1999 | Schuman |
| 6,126,633 A | 10/2000 | Kaji et al. |
| 6,139,563 A | 10/2000 | Cosgrove, III et al. |
| 6,174,280 B1 | 1/2001 | Oneda et al. |
| 6,206,893 B1 | 3/2001 | Klein et al. |
| 6,210,377 B1 | 4/2001 | Ouchi |
| 6,210,378 B1 | 4/2001 | Ouchi |
| 6,270,453 B1 | 8/2001 | Sakai |
| 6,551,238 B2 | 4/2003 | Staud |
| 6,554,845 B1 | 4/2003 | Fleenor et al. |
| 6,623,424 B2 | 9/2003 | Hayakawa et al. |
| 6,638,214 B2 | 10/2003 | Akiba |
| 6,656,195 B2 | 12/2003 | Peters et al. |
| 6,666,854 B1 | 12/2003 | Lange |
| 6,743,239 B1 | 6/2004 | Kuehn et al. |
| 6,752,756 B2 | 6/2004 | Lunsford et al. |
| 6,761,717 B2 | 7/2004 | Bales et al. |
| 6,997,931 B2 | 2/2006 | Sauer et al. |
| 7,147,650 B2 | 12/2006 | Lee |
| 7,364,582 B2 | 4/2008 | Lee |
| 2002/0045803 A1 | 4/2002 | Abe et al. |
| 2002/0095175 A1 | 7/2002 | Brock et al. |
| 2002/0133173 A1 | 9/2002 | Brock et al. |
| 2002/0156497 A1 | 10/2002 | Nagase et al. |
| 2002/0177750 A1 | 11/2002 | Pilvisto |
| 2002/0177847 A1 | 11/2002 | Long |
| 2003/0045900 A1 | 3/2003 | Hahnen et al. |
| 2003/0065359 A1 | 4/2003 | Weller et al. |
| 2003/0109898 A1 | 6/2003 | Schwarz et al. |
| 2003/0135204 A1 | 7/2003 | Lee et al. |
| 2003/0149338 A1 | 8/2003 | Francois et al. |
| 2003/0216618 A1 | 11/2003 | Arai |
| 2003/0233104 A1 | 12/2003 | Gellman et al. |
| 2004/0049205 A1 | 3/2004 | Lee et al. |
| 2004/0111009 A1 | 6/2004 | Adams et al. |
| 2004/0138529 A1 | 7/2004 | Wiltshire et al. |
| 2004/0176751 A1 | 9/2004 | Weitzner et al. |
| 2004/0193146 A1 | 9/2004 | Lee et al. |
| 2004/0236316 A1 | 11/2004 | Danitz et al. |
| 2005/0049580 A1 | 3/2005 | Brock et al. |
| 2005/0107667 A1 | 5/2005 | Danitz et al. |
| 2005/0228440 A1 | 10/2005 | Brock et al. |
| 2005/0251112 A1 | 11/2005 | Danitz et al. |
| 2005/0273084 A1 | 12/2005 | Hinman |
| 2005/0273085 A1 | 12/2005 | Hinman et al. |
| 2007/0221701 A1* | 9/2007 | Ortiz et al. .................. 227/175.1 |
| 2007/0276430 A1* | 11/2007 | Lee et al. ...................... 606/205 |
| 2008/0294191 A1* | 11/2008 | Lee ............... 606/205 |
| 2008/0312506 A1* | 12/2008 | Spivey et al. ................ 600/149 |

FOREIGN PATENT DOCUMENTS

| | | |
|---|---|---|
| EP | 0626604 A2 | 5/1994 |
| EP | 0427949 B1 | 6/1994 |
| GB | 2143920 | 2/1985 |

(56) References Cited

FOREIGN PATENT DOCUMENTS

| WO | WO 90/05491 | 5/1990 |
|---|---|---|
| WO | WO 92/01414 | 2/1992 |
| WO | WO 94/17965 | 8/1994 |
| WO | WO 94/22377 A | 10/1994 |
| WO | WO 2007/002545 A | 1/2007 |

OTHER PUBLICATIONS

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

Multi-DOF Forceps Manipulator System for Laparoscopic Surgery—Mechanism miniaturized & Evaluation of New Interfaces—Nakamura et al.

Multi-DOF Forceps Manipulator System for Laparoscopic Surgery—Nakamura et al.

Development of forceps manipulator system for laparoscopic surgery—Nakamura et al.

\* cited by examiner

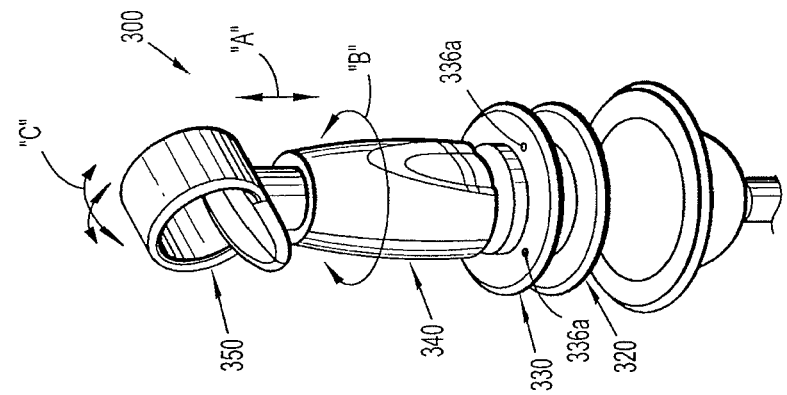
FIG. 8C
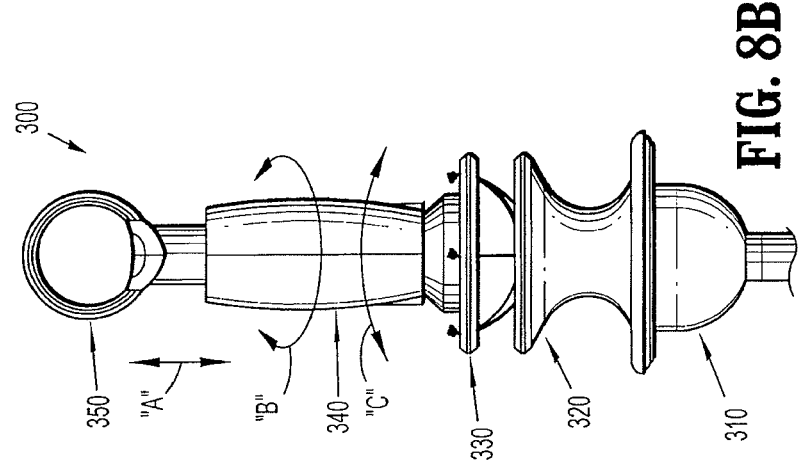
FIG. 8B
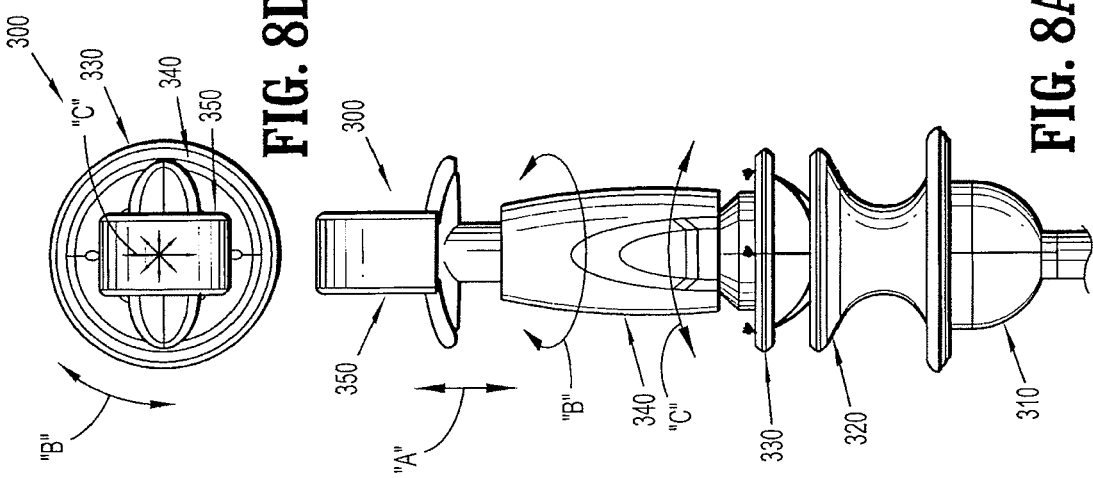
FIG. 8D
FIG. 8A

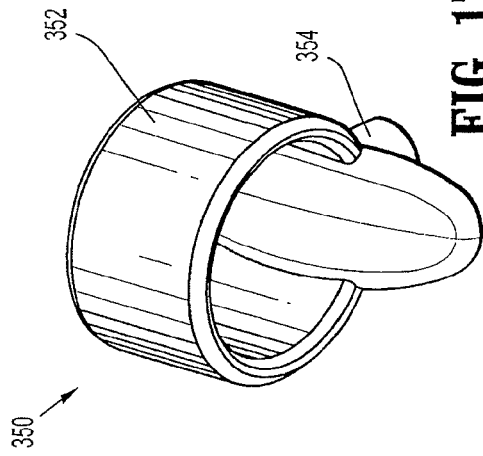
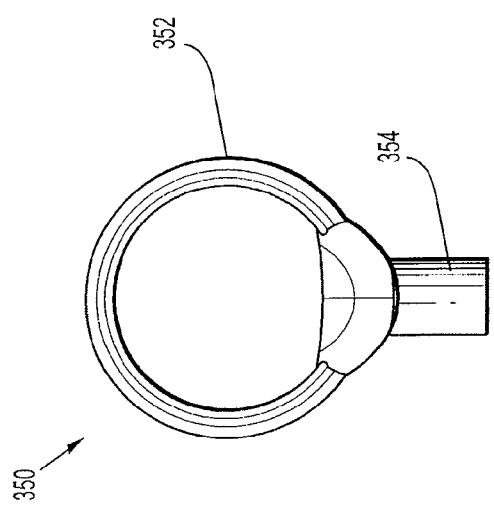
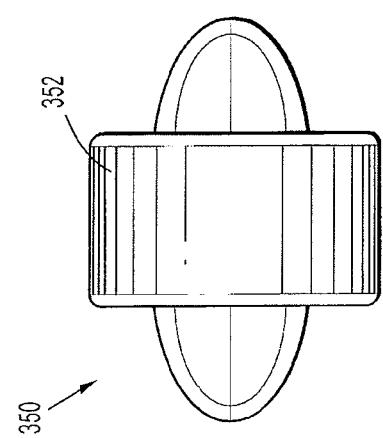
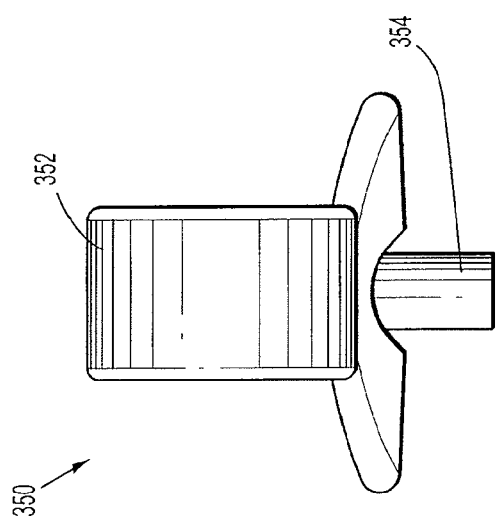
FIG. 17A
FIG. 17B
FIG. 17C
FIG. 17D

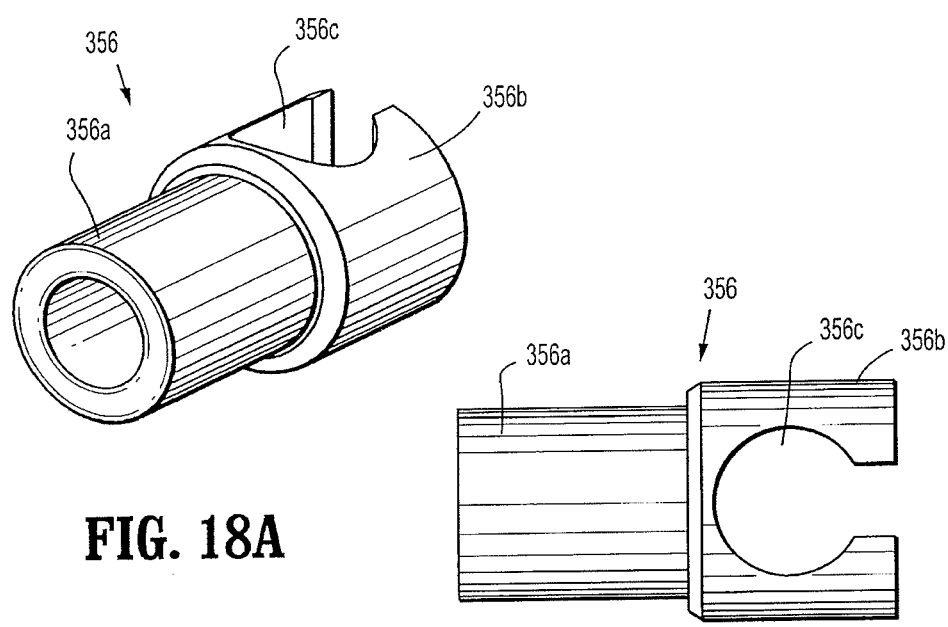
FIG. 18A
FIG. 18B
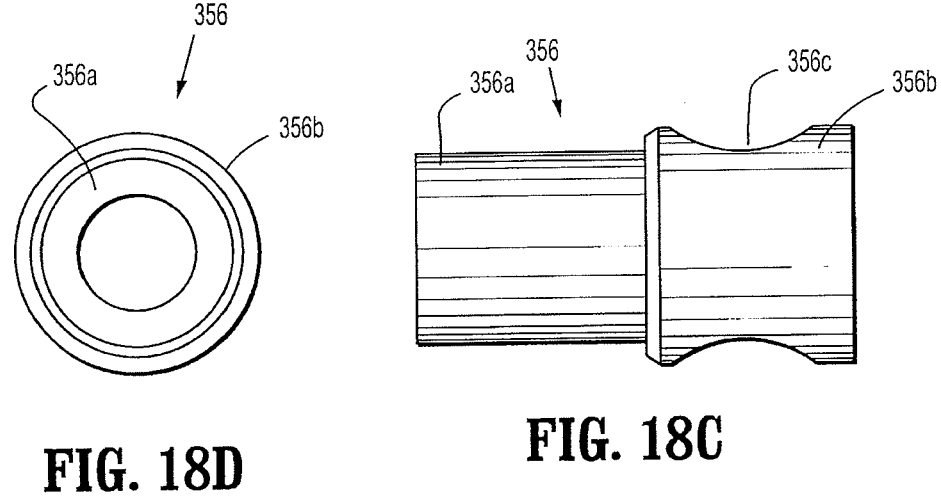
FIG. 18D
FIG. 18C

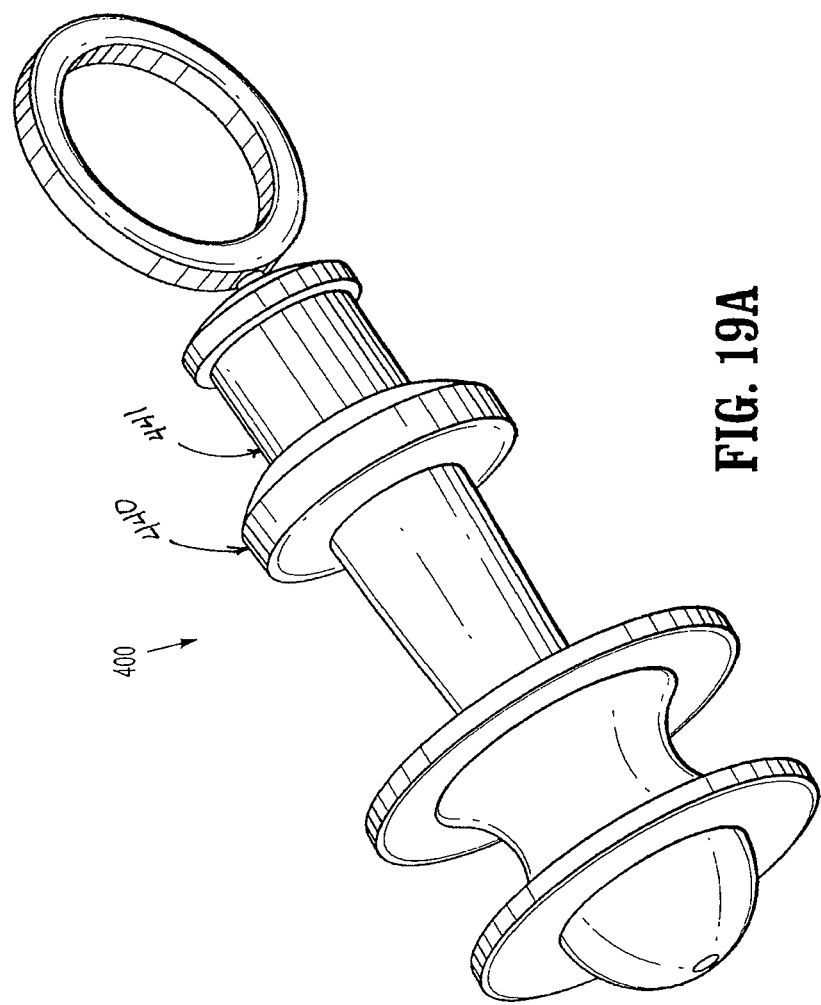

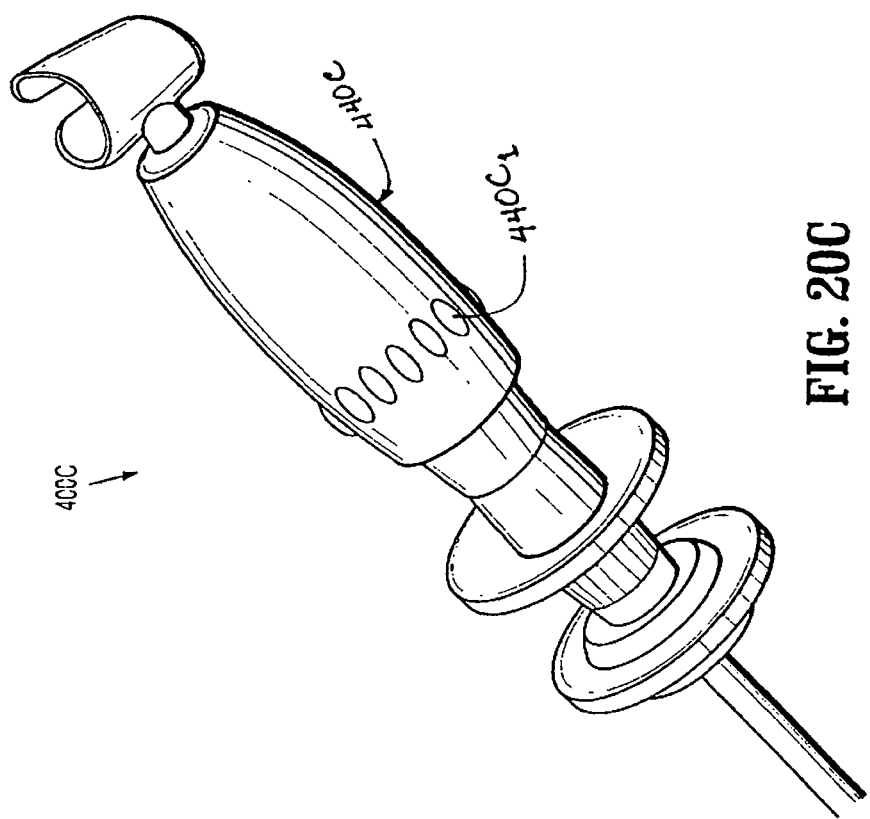

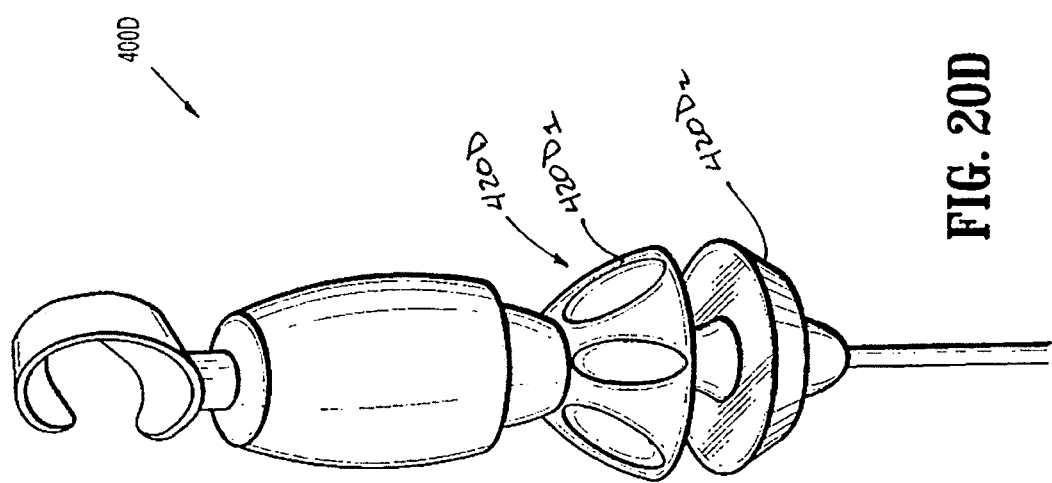

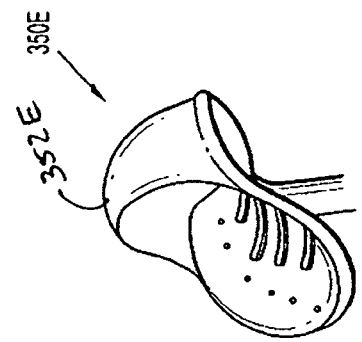
FIG. 21E
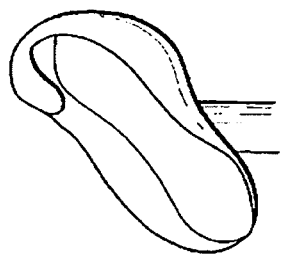
FIG. 21F
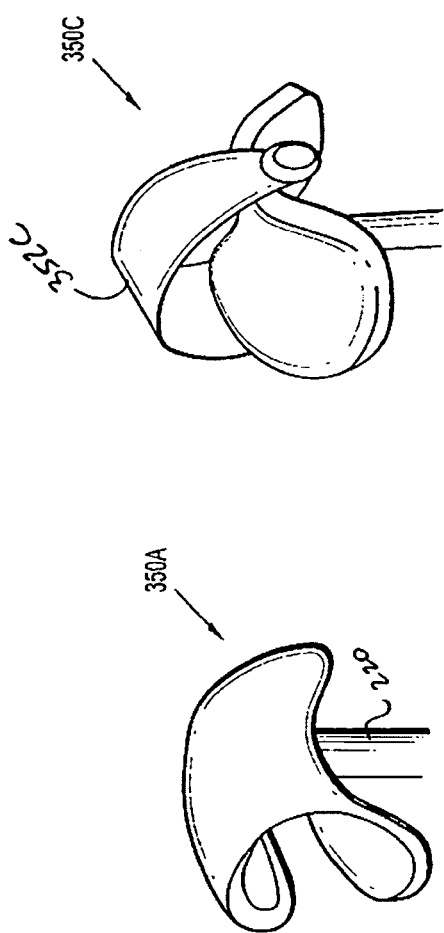
FIG. 21C
FIG. 21D
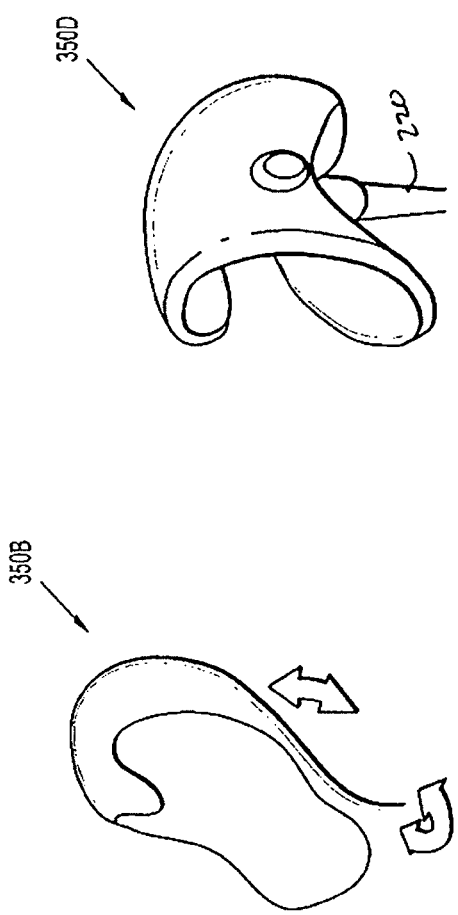
FIG. 21A
FIG. 21B

ENDOSCOPIC SURGICAL DEVICES

CROSS-REFERENCE TO RELATED APPLICATION

The present application claims the benefit of and priority to U.S. Provisional Application Ser. No. 60/965,857, filed on Aug. 23, 2007, the entire content of which is incorporated herein by reference.

BACKGROUND

1. Technical Field

The present disclosure relates to endoscopic surgical devices and, more particularly, to endoscopic surgical graspers and the like capable of a multitude of degrees of operation and/or movement.

2. Background of Related Art

Endoscopic surgery is surgery performed intracorporeally without requiring a large incision. Endoscopic surgery is typically performed by inserting a number of ports through small incisions in the patient's skin to access the surgical site. One of the ports receives an endoscope, which is a video camera-like device. The surgeon views the surgical site via the endoscope and performs the surgery by inserting various surgical devices through the ports into the patient. This avoids having to "open up" the patient, resulting in less invasive surgery than conventional procedures. One such surgical device includes a hand operated endoscopic grasper.

In an effort to reduce the number of incisions made into the patient, single incision procedures and related surgical devices are being developed. Accordingly, providing surgical devices capable of a multitude of degrees of operation is desirable.

Accordingly, a need exists for surgical devices including multiple degrees of operation and degrees of motion.

SUMMARY

The present disclosure relates to endoscopic surgical devices, including graspers and the like, capable of a multitude of degrees of operation and/or movement.

According to an aspect of the present disclosure, an endoscopic surgical device is provided and includes a handle assembly; a tube assembly operatively supported on and extending from the handle assembly, the tube assembly defining a longitudinal axis; an articulation assembly operatively supported on and extending from a distal end of the tube assembly; and a tool assembly operatively supported on and extending from a distal end of the articulation assembly. The handle assembly is connected to the tool assembly in such a manner such that a rotation of the handle assembly about the longitudinal axis results in a concomitant rotation of the tool assembly. The handle assembly is connected to the tool assembly in such a manner that an actuation of the handle assembly in a particular manner results in a concomitant actuation of the tool assembly. The handle assembly is connected to the tool assembly in such a manner that a pivoting of the handle assembly in any off-axis direction relative to the longitudinal axis results in a concomitant articulation of the tool assembly via the articulation assembly.

The tube assembly may include an outer tube and an inner shaft supported in the outer tube, wherein the inner shaft is capable of rotation and translation relative to the outer tube. The handle assembly may include a collar connected to the inner shaft, wherein a rotation of the collar results in a concomitant rotation of the shaft.

The tool assembly may be connected to a distal end of the inner shaft such that the rotation of the collar results in the concomitant rotation of the tool assembly.

The articulation assembly may include a plurality of joints operatively connected to one another, wherein the plurality of joints includes at least one knuckle permitting articulation in a first transverse direction relative to the longitudinal axis, and at least one knuckle permitting articulation in a second transverse direction relative to the longitudinal axis. The at least one knuckle permitting articulation in a first direction and the at least one knuckle permitting articulation in a second direction may be oriented substantially orthogonal to one another.

The handle assembly may include a ball joint configured for radial articulation in any direction around the longitudinal axis, and a plurality of articulation cables each having a first end connected to the ball joint and each having a second end extending through the tube assembly and the articulation assembly and connected to the tool assembly. In use, tilting of the handle assembly about the ball joint, relative to the longitudinal axis, may result in concomitant articulation of the tool assembly.

At least four evenly spaced articulation cables may be provided around a central axis of the tube assembly. In use, as the handle is tilted off-axis, the ball joint exerts a force in a proximal direction on at least one of said plurality of articulation cables resulting in the concomitant articulation of the tool assembly.

The tool assembly may include a pair of juxtaposed jaws. A distal end of the inner shaft may be operatively connected to the jaws such that a reciprocation of inner shaft relative to the outer tube may result in an opening and closing of the jaws, and a rotation of the inner shaft relative to the outer tube may result in a rotation of the jaws.

Each jaw may define a cam slot therein. The tool assembly may include a cam pin slidably disposed within each cam slot defined in the jaws. The cam pin may be connected to the inner shaft such that translation of the inner shaft results in translation of the cam pin through the cam slots.

The handle assembly may further include an actuator connected to the inner shaft. In use, actuation of the actuator may result in translation of the inner shaft relative to the outer tube.

The handle assembly may include a keyed member secured to the inner shaft and defining at least one outer longitudinally extending groove, and wherein the collar may include at least one corresponding guide projecting into a respective groove of the keyed member. In use, rotation of the collar may impart rotation to keyed member and the inner shaft and wherein the keyed member and the inner shaft may be axially translatable relative to the collar.

The handle assembly may include a spool defining a central lumen therethrough and an off-set lumen for each of said plurality of articulation cables. The spool may define a concave proximal surface configured for engagement with the ball joint. The spool may define a concave annular outer surface.

The inner shaft may be bendable and may be capable of transmitting rotational forces and axial forces.

According to another aspect of the present disclosure, an endoscopic surgical device is provided and includes a handle assembly defining a longitudinal axis. The handle assembly includes an articulation joint configured for off-axis tilting relative to the longitudinal axis; a rotation collar configured for rotation about the longitudinal axis, the rotation collar having a keyed member disposed therein, wherein the collar and the keyed member are connected to one another such that rotation of the collar transmits rotation to the keyed member and such that the keyed member is axially movable relative to the collar; and an actuation member configured for axial translation along the longitudinal axis. The endoscopic surgical device further includes a tube assembly operatively supported on and extending from the handle assembly. The tube assembly includes a fixed outer tube; and an inner shaft slidably and rotatably disposed in the outer tube, the inner shaft being connected to the keyed member and the actuation member, wherein rotation of the collar results in rotation of the inner shaft and axial translation of the actuation member results in axial translation of the inner shaft. The endoscopic surgical device further includes an articulation assembly operatively supported on and extending from a distal end of the tube assembly, wherein the articulation assembly is configured for articulation in at least two axes transverse to the longitudinal axis, wherein the articulation assembly is controlled by the tilting of the articulation joint. The endoscopic surgical device further includes a tool assembly operatively supported on and extending from a distal end of the articulation assembly, wherein a distal end of the inner shaft is connected to the tool assembly such that axial translation of the inner shaft results in a first operation of the tool assembly and rotation of the inner shaft results in a second operation of the tool assembly.

The articulation assembly may include a plurality of joints operatively connected to one another, wherein the plurality of joints includes at least one knuckle permitting articulation in a first transverse direction relative to the longitudinal axis, and at least one knuckle permitting articulation in a second transverse direction relative to the longitudinal axis. The at least one knuckle permitting articulation in a first direction and the at least one knuckle permitting articulation in a second direction may be oriented substantially orthogonal to one another.

The articulation joint may be a ball joint configured for radial articulation in any direction around the longitudinal axis. The handle assembly may include a plurality of articulation cables each having a first end connected to the ball joint and each having a second end slidably extending through the tube assembly and the articulation assembly and being connected to the tool assembly. In use, tilting of the handle assembly about the ball joint, relative to the longitudinal axis, may result in concomitant articulation of the tool assembly.

The endoscopic surgical device may include at least four evenly spaced articulation cables are provided around a central axis of the tube assembly. In use, as the handle is tilted off-axis, the ball joint exerts a force in a proximal direction on at least one of said plurality of articulation cables resulting in the concomitant articulation of the tool assembly.

The tool assembly may include a pair of juxtaposed jaws, wherein a distal end of the inner shaft is operatively connected to the jaws such that a reciprocation of inner shaft relative to the outer tube results in an opening and closing of the jaws, and a rotation of the inner shaft relative to the outer tube results in a rotation of the jaws. Each jaw may define a cam slot therein and wherein a cam pin is slidably disposed within each cam slot defined in the jaws, and wherein the cam pin is connected to the inner shaft such that translation of the inner shaft results in translation of the cam pin through the cam slots.

The keyed member may define at least one outer longitudinally extending groove and wherein the collar may include at least one corresponding guide projecting into a respective groove of the keyed member. In use, rotation of the collar may impart rotation to keyed member and the inner shaft. The keyed member and the inner shaft may be axially translatable relative to the collar.

The handle assembly may include a spool defining a central lumen therethrough and an off-set lumen for each of said plurality of articulation cables. The spool may define a concave proximal surface configured for engagement with the ball joint. The spool may define a concave annular outer surface.

The inner shaft may be bendable and may be capable of transmitting rotational forces and axial forces.

According to yet another embodiment of the present disclosure, an endoscopic surgical device is provided and includes a handle assembly defining a longitudinal axis. The handle assembly includes an articulation joint configured for omni-directional off-axis tilting relative to the longitudinal axis; a rotation collar configured for rotation about the longitudinal axis; and an actuation member configured for axial translation along the longitudinal axis. The endoscopic surgical device further includes a tube assembly operatively supported on and extending from the handle assembly. The tube assembly includes a fixed outer tube; and an inner shaft slidably and rotatably disposed in the outer tube. The inner shaft is connected to the collar and the actuation member such that rotation of the collar results in rotation of the inner shaft and axial translation of the actuation member results in axial translation of the inner shaft. The endoscopic surgical device further includes an articulation assembly operatively supported on and extending from a distal end of the tube assembly, wherein the articulation assembly is configured for omni-directional articulation concomitant with the omni-directional tilting of the articulation joint. The endoscopic surgical device further includes a tool assembly operatively supported on and extending from a distal end of the articulation assembly, wherein a distal end of the inner shaft is connected to the tool assembly such that axial translation of the inner shaft results in a first operation of the tool assembly and rotation of the inner shaft results in a second operation of the tool assembly.

The rotation collar may include a keyed member disposed therein. The collar and the keyed member may be connected to one another such that rotation of the collar transmits rotation to the keyed member and such that the keyed member is axially movable relative to the collar. The inner shaft may be connected to the keyed member and the actuation member.

The articulation assembly may include a plurality of joints operatively connected to one another, wherein the plurality of joints includes at least one knuckle permitting articulation in a first transverse direction relative to the longitudinal axis, and at least one knuckle permitting articulation in a second transverse direction relative to the longitudinal axis. The at least one knuckle permitting articulation in a first direction and the at least one knuckle permitting articulation in a second direction may be oriented substantially orthogonal to one another.

The articulation joint may be a ball joint. The handle assembly may include a plurality of articulation cables each having a first end connected to the ball joint and each having a second end slidably extending through the tube assembly and the articulation assembly and being connected to the tool assembly. In use, tilting of the handle assembly in any direction about the ball joint, relative to the longitudinal axis, may result in concomitant articulation of the tool assembly.

At least four evenly spaced articulation cables may be provided around a central axis of the tube assembly. In use, as the handle is tilted off-axis, the ball joint may exert a force in a proximal direction on at least one of said plurality of articulation cables resulting in the concomitant articulation of the tool assembly.

The tool assembly may include a pair of juxtaposed jaws. A distal end of the inner shaft may be operatively connected to the jaws such that a reciprocation of inner shaft relative to the outer tube may result in an opening and closing of the jaws, and a rotation of the inner shaft relative to the outer tube may result in a rotation of the jaws. Each jaw may define a cam slot therein. A cam pin may be slidably disposed within each cam slot defined in the jaws, and wherein the cam pin may be connected to the inner shaft such that translation of the inner shaft results in translation of the cam pin through the cam slots.

The keyed member may define at least one outer longitudinally extending groove and wherein the collar may include at least one corresponding guide projecting into a respective groove of the keyed member. In use, rotation of the collar may impart rotation to keyed member and the inner shaft. The keyed member and the inner shaft may be axially translatable relative to the collar.

The handle assembly may include a spool defining a central lumen therethrough and an off-set lumen for each of said plurality of articulation cables. The spool may define a concave proximal surface configured for engagement with the ball joint. The spool may define a concave annular outer surface.

The inner shaft may be bendable and may be capable of transmitting rotational forces and axial forces.

DETAILED DESCRIPTION OF THE DRAWINGS

The present surgical devices will be more fully appreciated as the same becomes better understood from the following detailed description when considered in connection with the following drawings, in which:

FIGS. 8A-8D are illustrations of the handle assembly of FIG. 1;

FIGS. 17A-17D are illustrations of a thumb actuator of the handle assembly of FIGS. 8A-8D;

FIGS. 18A-18D are illustrations of a socket joint of the handle assembly of FIGS. 8A-8D;

FIGS. 19A-19F are illustrations of a handle assembly according to an alternate embodiment of the present disclosure;

FIGS. 20A-20J are illustrations of various handle assemblies according to the present disclosure; and FIGS. 21A-21F are illustrations of various actuators of the present disclosure.

DETAILED DESCRIPTION OF EMBODIMENTS

Figure 1A:
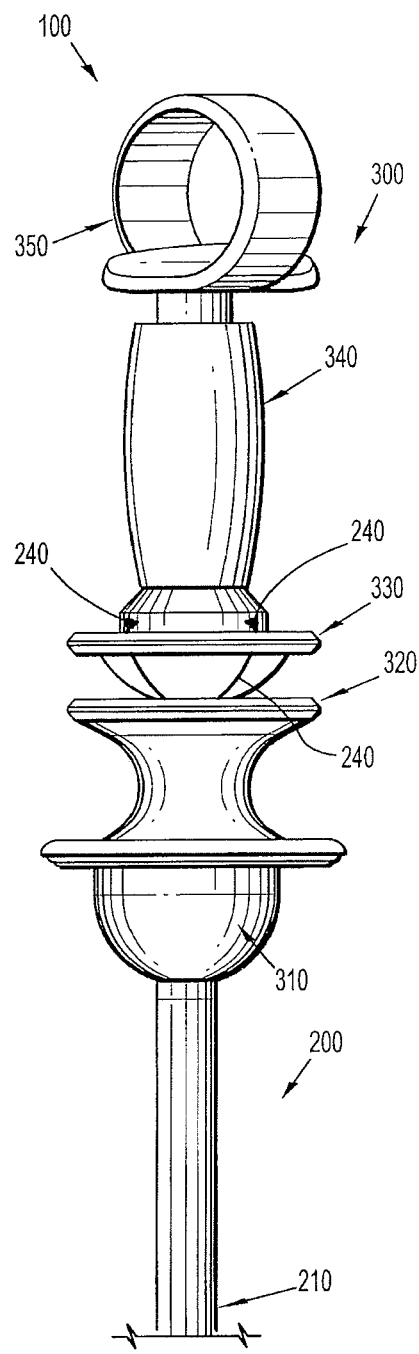
FIG. 1A is a perspective view of a handle assembly of an endoscopic surgical device of the present disclosure, shown in a straight or un-articulated position.

Embodiments of surgical devices in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the device which is closer to the user and the term "distal" refers to the end of the device which is further away from the user.

Figure 1B:
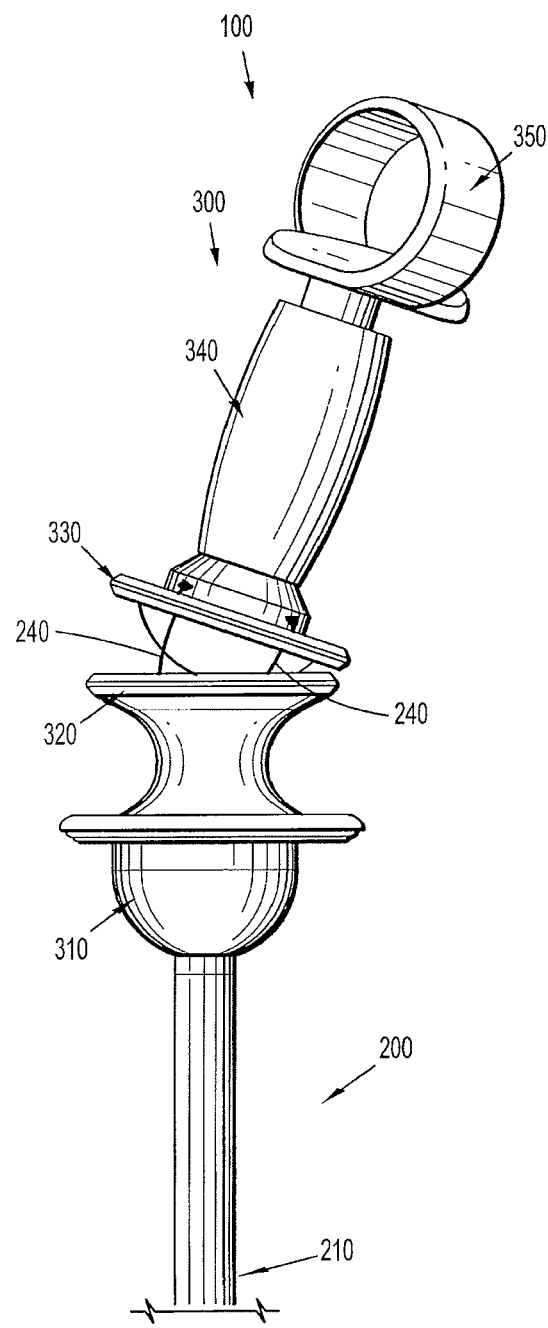
FIG. 1B is a perspective view of the handle assembly of FIG. 1A, shown in a canted or articulated position.

Referring initially to FIGS. 1A-3, an endoscopic surgical device is generally designated as 100. Surgical device 100 includes an endoscopic assembly 200 (see FIG. 2A-3) operatively connected to and extending from a handle assembly 300 (see FIGS. 1A and 1B). In general, as seen in FIG. 1, handle assembly 300 may be configured so as to be held in a hand of an operator in the manner of a syringe or the like and is configured to be operated, if desired, solely with said hand.

Endoscopic assembly 200 includes a proximal outer tube 210 having a proximal end secured to and extending from handle assembly 300, an articulation assembly 230 supported on and extending from a distal end of the proximal outer tube 210, and a distal outer tube 220 supported on and extending from a distal end of the articulation assembly 230. Endoscopic assembly 200 further includes an inner shaft (not shown), (e.g., a flexible cable or wire) that is slidably and rotatably supported within and extending through proximal outer tube 210, articulation assembly 230 and distal outer tube 220. A proximal end of inner shaft extends into handle assembly 300 and a distal end of inner shaft extends from a distal end of distal outer tube 220 and is operatively connected to a jaw assembly 250.

Endoscopic assembly 200 includes an inner tube 250 supported in distal outer tube 220 and configured to surround the inner shaft. A distal end of inner tube 250 defines a clevis which is configured to pivotably support the jaw assembly 260. Jaw assembly 260 includes a pair of jaw members 262, 264 each defining a cam slot (not shown) configured to slidably receive a cam pin (not shown) therethrough. The cam pin is supported on a distal end of the inner shaft and extends from opposite sides thereof to slidably translate in guide slots (not shown) formed in the arms of the clevis. In this manner, as inner shaft is translated relative to inner tube 250, jaw assembly 260 is caused to be open and closed. Jaw members 262, 264 may be configured to grasp tissue and/or cut tissue.

As seen in FIGS. 2A-2C and 4A-7D, articulation assembly 230 includes at least a pair of joints 232, 234 configured for pivotable movement relative to one another. Each joint 232, 234 includes a respective knuckle 232a, 234a and a respective clevis 232b, 234b formed therewith. Each knuckle operatively engages a clevis of an adjacent joint so as to define a pivot axis. Each joint 232, 234 defines a respective central lumen 232c, 234c formed therethrough for receipt of the inner shaft therein and two-pair of diametrically opposed lumens 232d, 234d formed around central lumen 232c, 234c. Articulation cables 240 are provided and slidably extend through lumens 232c, 234c of joints 232, 234.

Articulation assembly 230 includes a proximal support joint 236 supported at the distal end of proximal outer tube 210 and defining a clevis 236b configured to pivotably engage a knuckle of joints 232, 234, and a distal support joint 238 supported at a proximal end of distal outer tube 220 and defining a knuckle 238a configured to pivotably engage a clevis of joints 232, 234. Each support joint 236, 238 includes two-pair of diametrically opposed lumens 236d, 238d formed around a central lumen 236c, 238c thereof. Each support joint 236, 238 further includes a stem 236e, 238e for receipt in respective proximal outer tube 210 and distal outer tube 220.

Figure 2A:
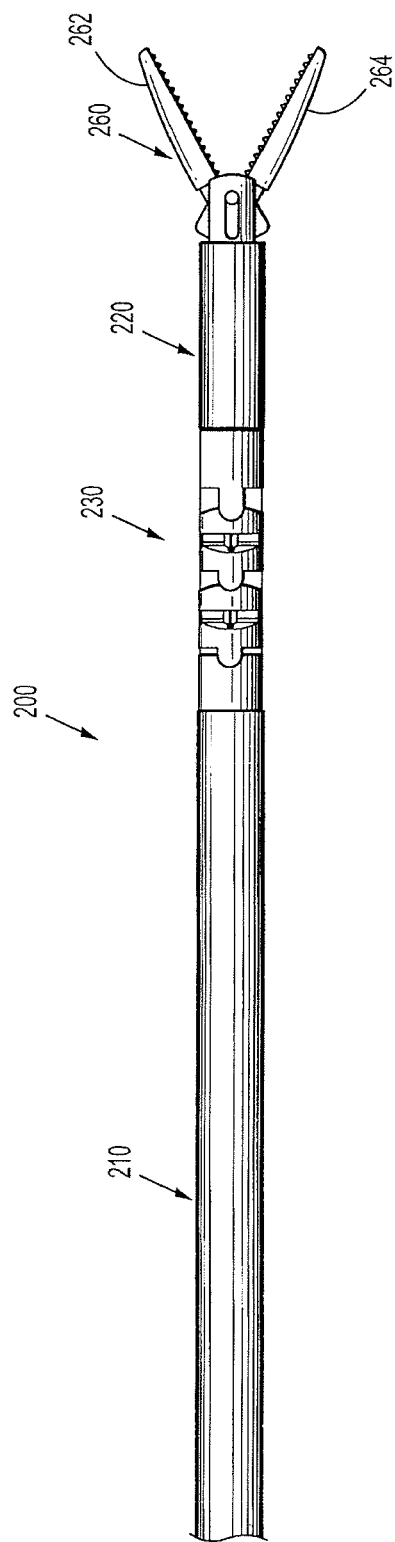
FIGS. 2A-2C are perspective views of the endoscopic assembly of the endoscopic surgical device of the present disclosure, shown in various angles of articulation.
Figure 2B:
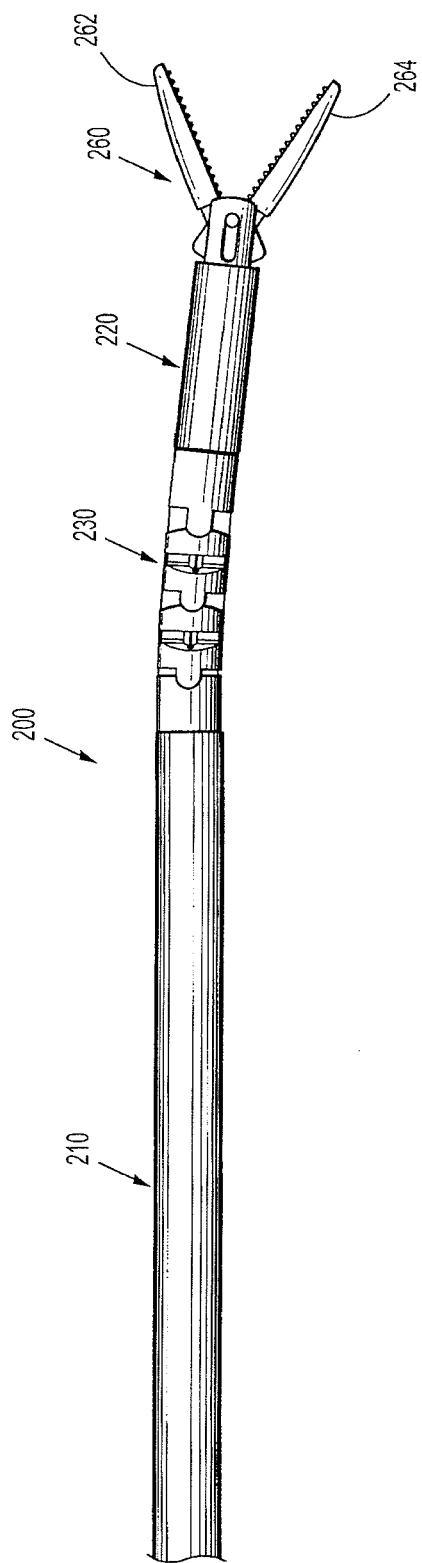
Figure 2C:
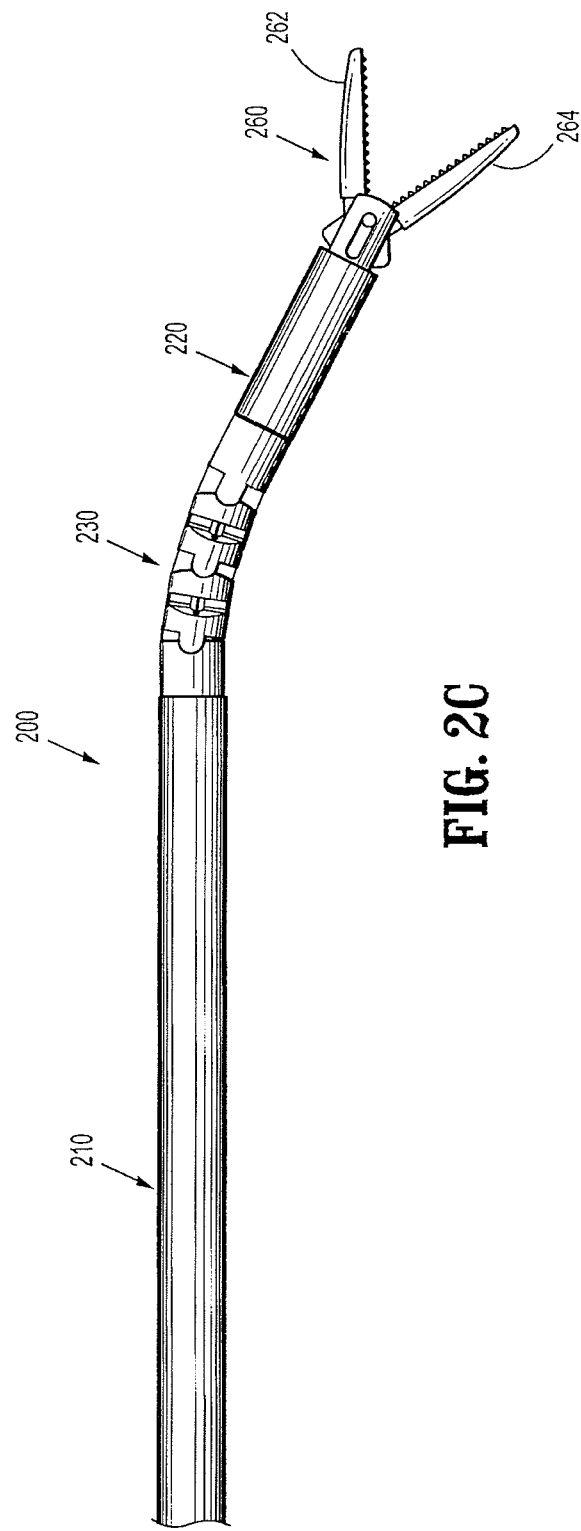
Figure 3:
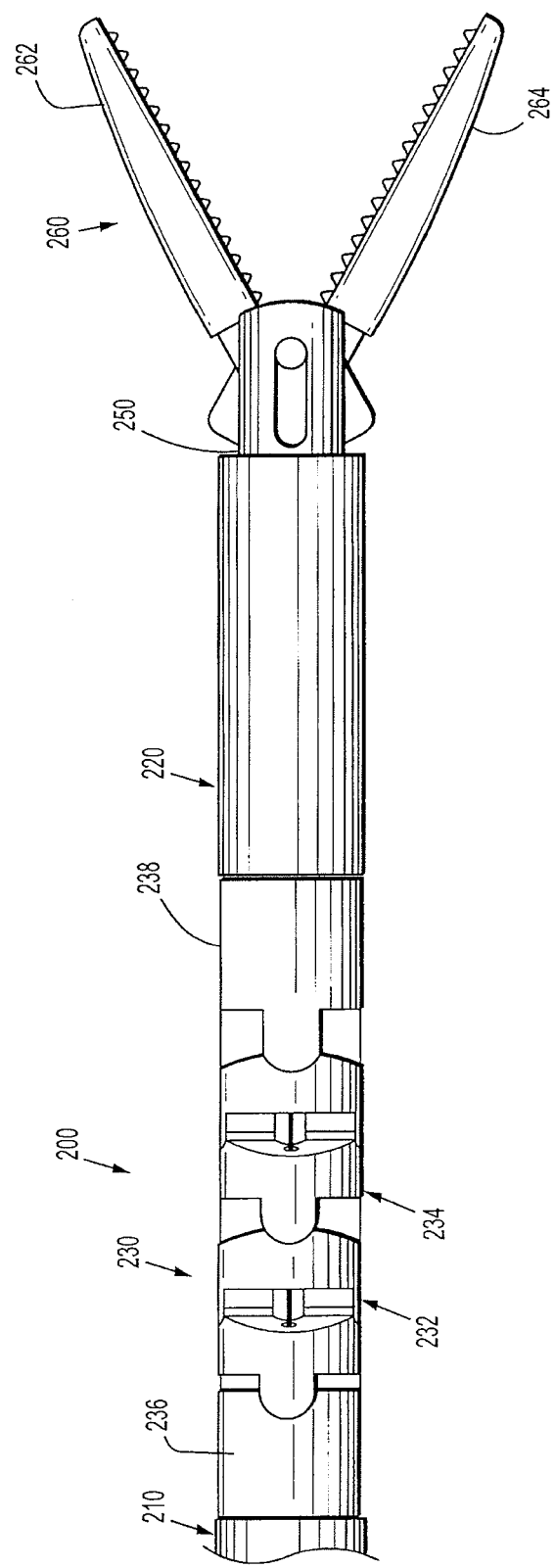
FIG. 3 is an enlarged view of the distal end of the endoscopic assembly of FIGS. 2A-2C.
Figure 4A:
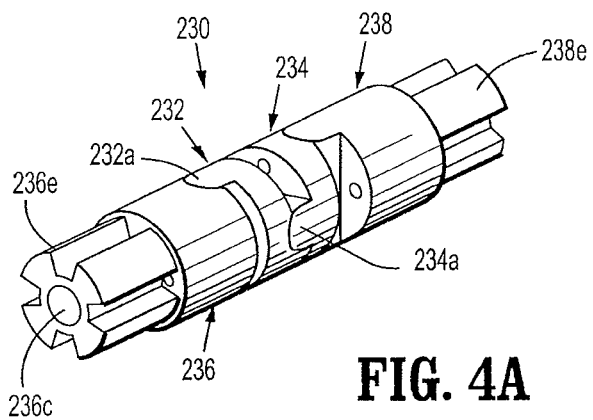
FIGS. 4A-4D are illustrations of an articulation joint of the endoscopic assembly of FIGS. 2A-2C.
Figure 4B:
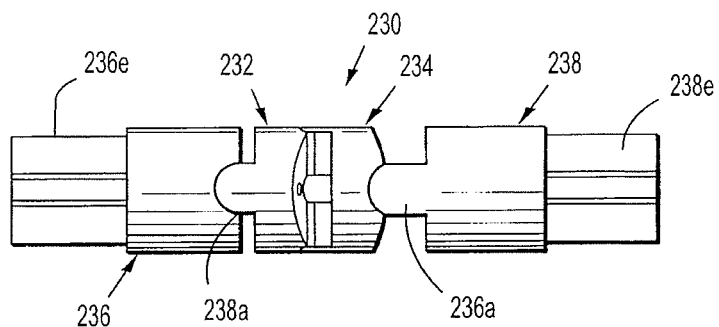
Figure 4D:
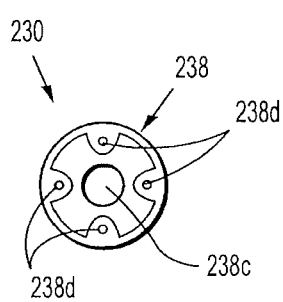
Figure 4C:
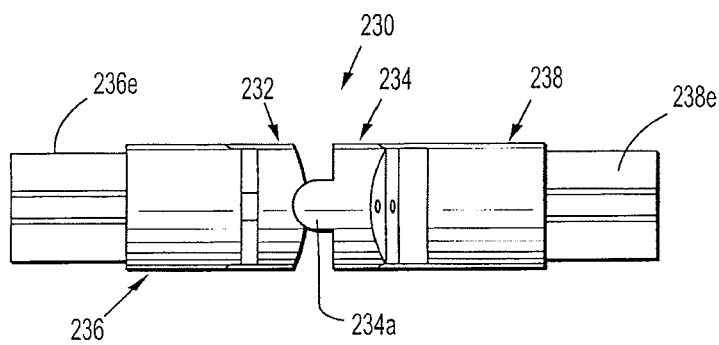
Figure 5A:
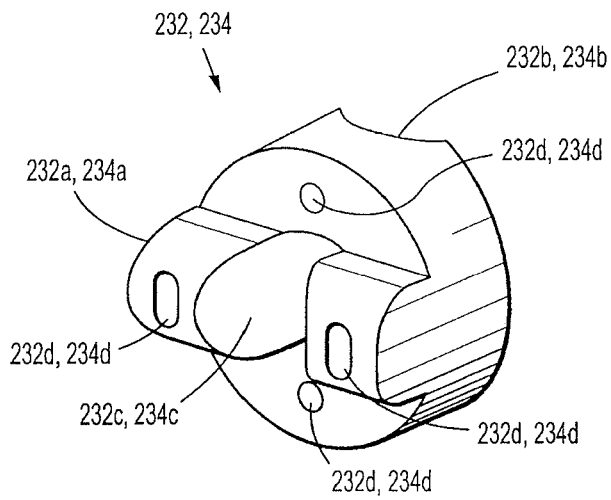
FIGS. 5A-5D are illustrations of a knuckle of the articulation joint of FIGS. 4A-4D.
Figure 5B:
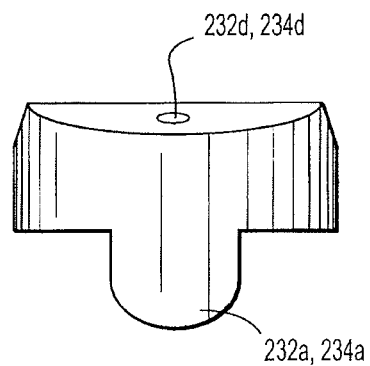
Figure 5D:
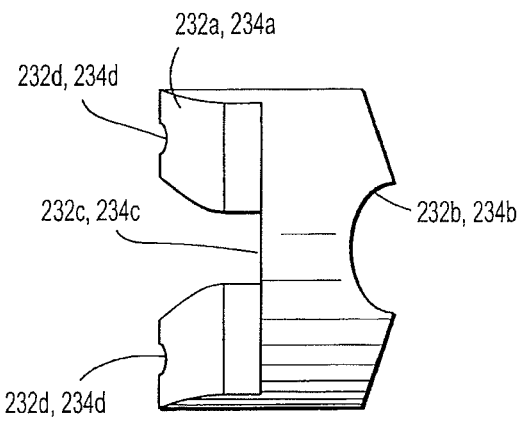
Figure 5C:
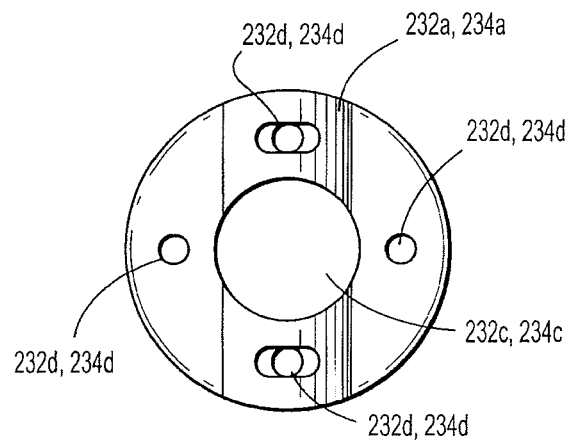
Figure 6A:
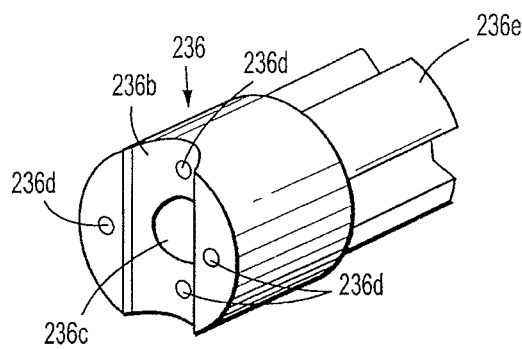
FIGS. 6A-6D are illustrations of a first connector of the articulation joint of FIGS. 4A-4D.
Figure 6B:
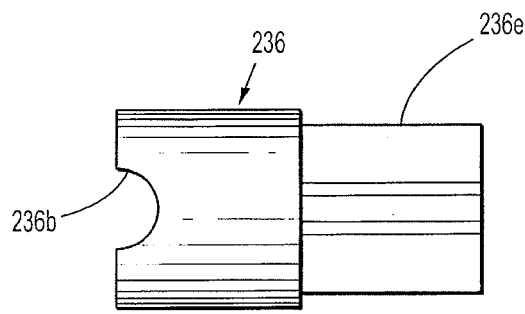
Figure 6D:
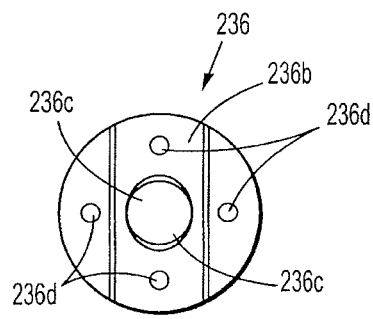
Figure 6C:
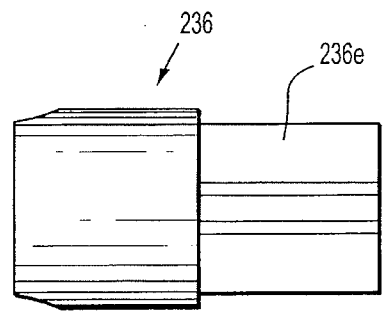
Figure 7A:
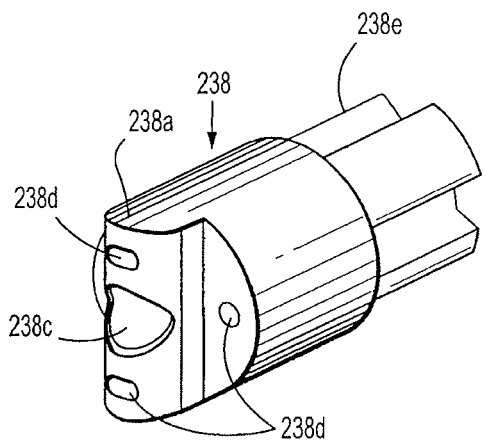
FIGS. 7A-7D are illustrations of a second connector of the articulation joint of FIGS. 4A-4D.
Figure 7B:
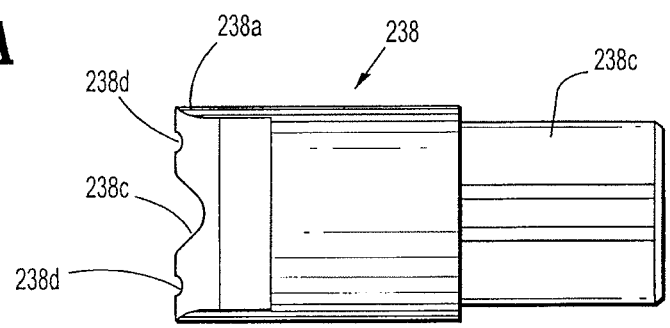
Figure 7D:
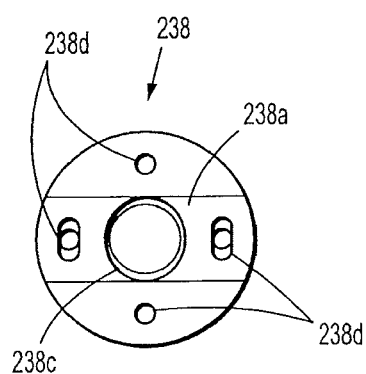
Figure 7C:
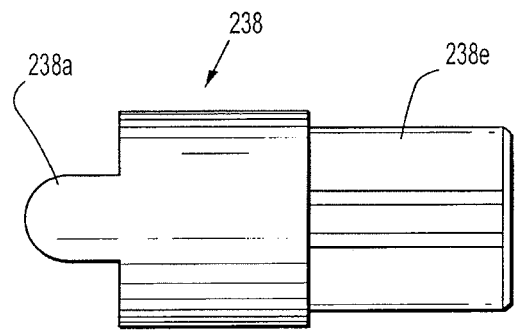
Figure 9A:
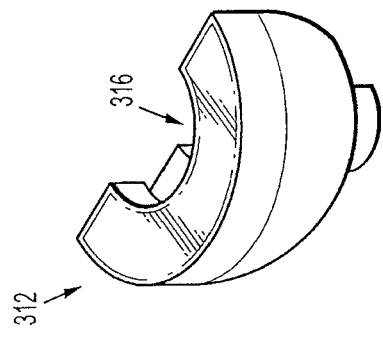
FIGS. 9A-9D are illustrations of a first half-section of a hub of the handle assembly of FIGS. 8A-8D.
Figure 9E:
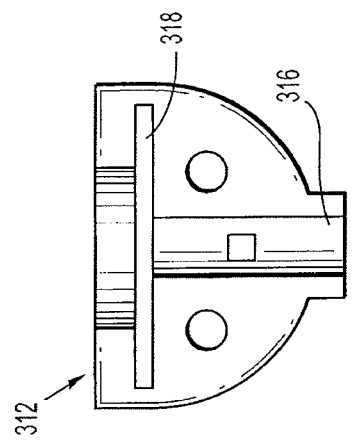
Figure 9D:
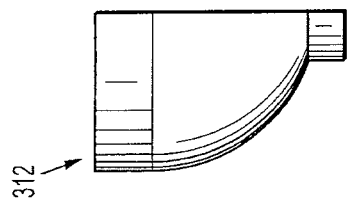
Figure 9B:
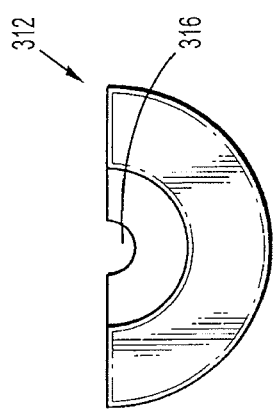
Figure 9C:
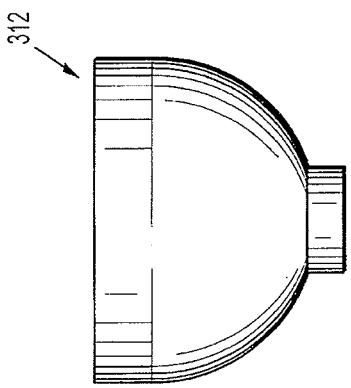
Figure 10A:
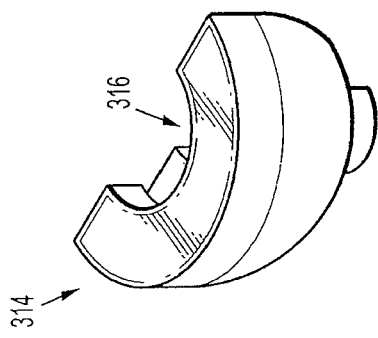
FIGS. 10A-10D are illustrations of a second half-section of the hub of the handle assembly of FIGS. 8A-8D.
Figure 10E:
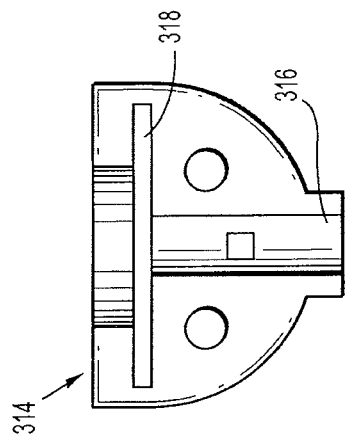
Figure 10D:
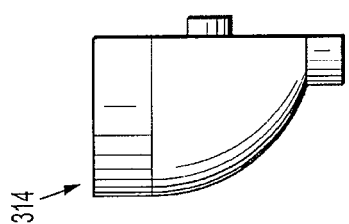
Figure 10B:
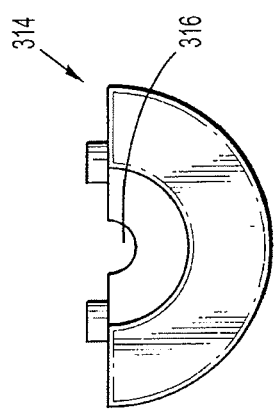
Figure 10C:
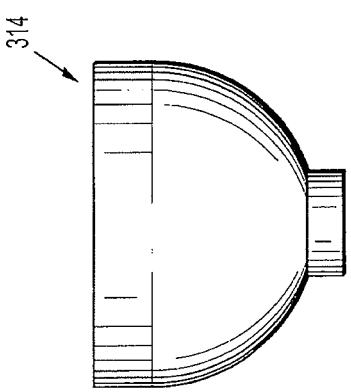

The knuckles and clevis pair may be alternatingly oriented orthogonal to an adjacent knuckle/clevis pair so as to enable articulation joint 230 to articulate in at least two degrees, i.e., in the plane of the page as seen in FIGS. 2B and 2C, and out of the plane of the page (not shown). It is contemplated that any number of joints 232, 234 may be provided as needed or desired. It is understood that the greater the number of joints provided the greater the degree of articulation of the distal end of endoscopic device 100.

As seen in FIGS. 1A, 1B and 8A-18D, handle assembly 300 includes a hub 310 operatively connected to a proximal end of proximal outer tube 210, a spool 320 operatively supported on and/or connected to hub 310, a ball joint 330 operatively supported on and/or connected to spool 320, a collar 340 operatively supported on and/or connected to ball joint 330; and an actuator 350 operatively supported in and through collar 340.

As seen in FIGS. 9A-10E, hub 310 may be formed in a pair of halves 312, 314 which are joined to one another so as to support the proximal end of the proximal outer tube therebetween. When joined together, halves 312, 314 define a lumen 316 therethrough and an annular recess 318 therewithin.

Figure 11A:
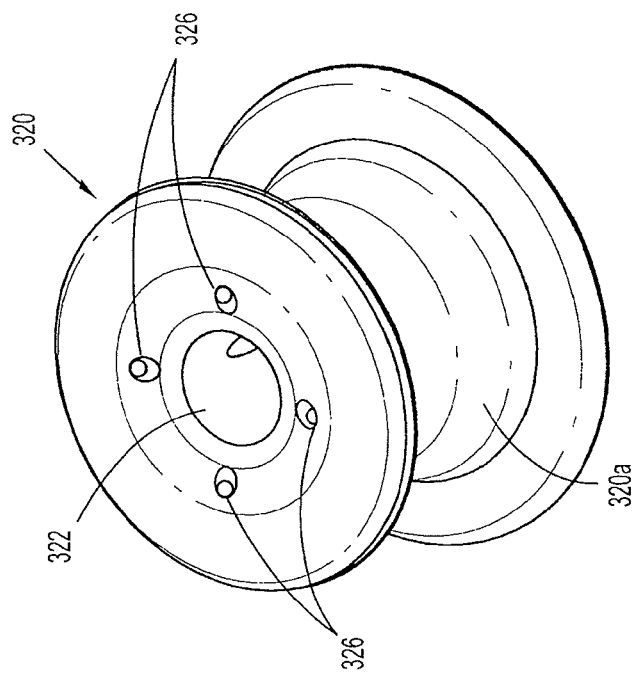
FIGS. 11A-11C are illustrations of a spool of the handle assembly of FIGS. 8A-8D.
Figure 11B:
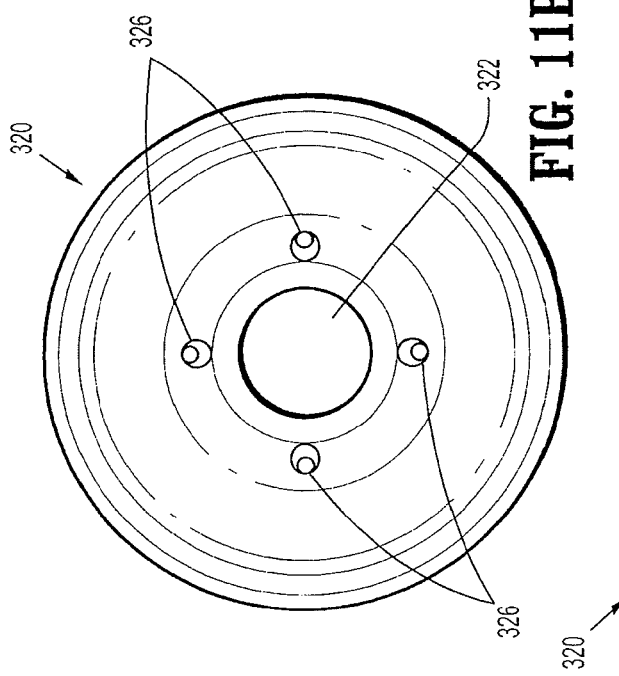
Figure 11C:
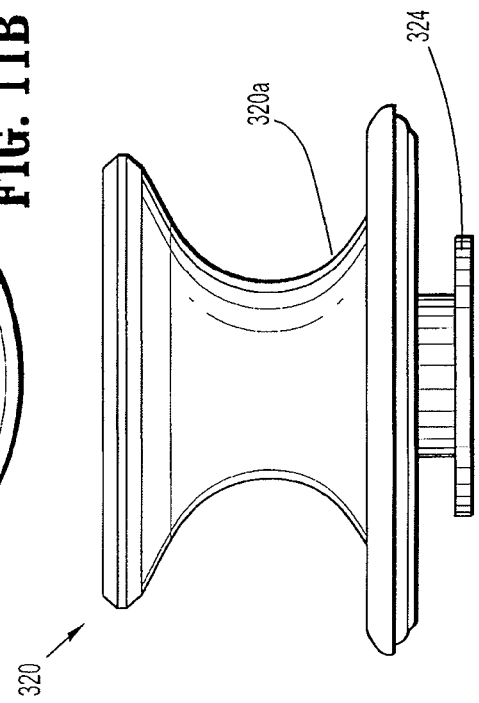
Figure 12A:
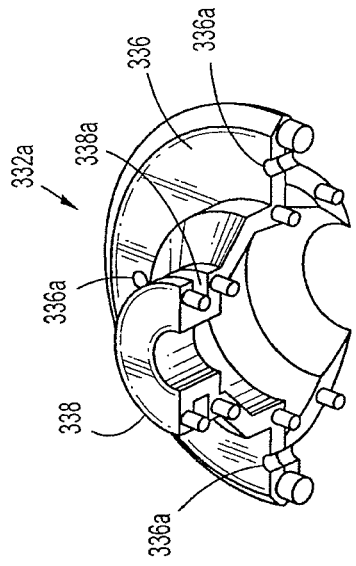
FIGS. 12A-12D are illustrations of a first half-section of a ball joint of the handle assembly of FIGS. 8A-8D.
Figure 12B:
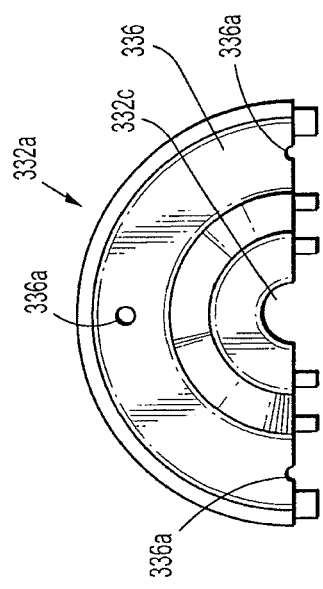
Figure 12D:
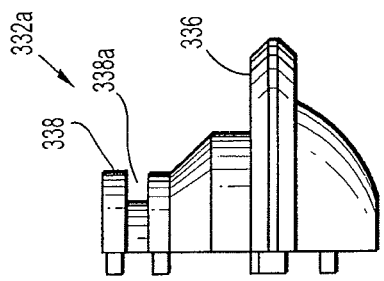
Figure 12C:
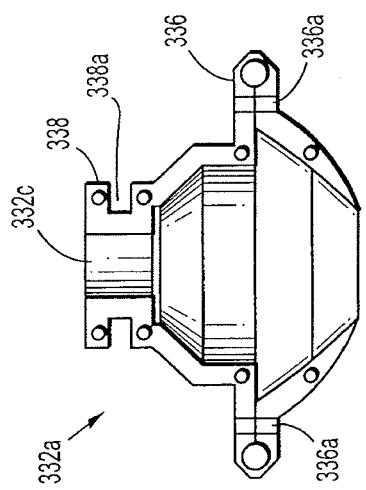
Figure 13A:
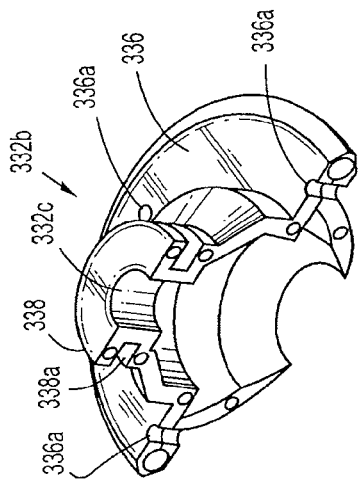
FIGS. 13A-13E are illustrations of a second half-section of the ball joint of the handle assembly of FIGS. 8A-8D.
Figure 13E:
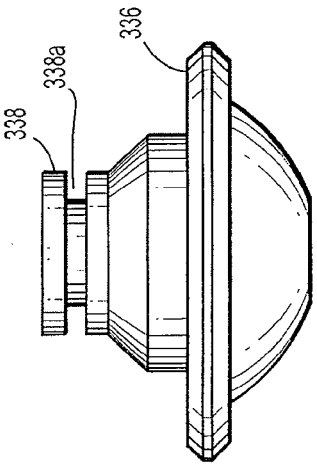
Figure 13D:
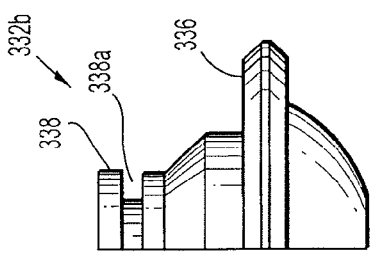
Figure 13B:
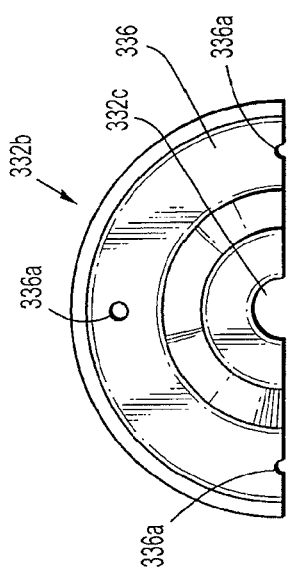
Figure 13C:
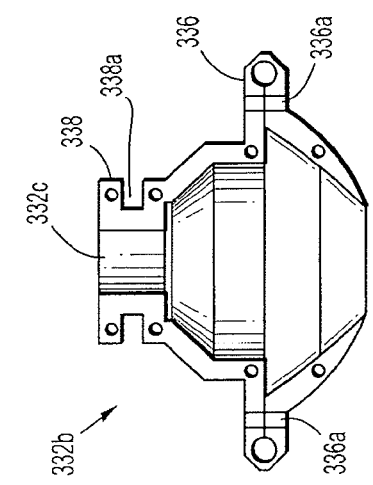

As seen in FIGS. 1A, 1B and 11A-11C, spool 320 defines a concave outer annular side-wall profile 320a and a lumen 322 extending therethrough. The concavity of the profile of the side-wall may be such so as to accommodate a digit of the hand of the user, such as for example the middle and ring fingers on other side thereof. As seen in FIG. 11C, spool 320 includes a flange 324 extending from a distal surface thereof. Flange 324 is configured and dimensioned for receipt in annular recess 318 of hub 310. In this manner, when halves 312, 314 of hub 310 are joined together, flange 324 is contained within annular recess 318 of hub 310. It is contemplated that annular recess 318 of hub 310 and flange 324 of spool 320 may be dimensioned such that spool 320 is free to rotate relative to hub 310.

As seen in FIGS. 11A and 11B, a proximal surface of spool 320 may have a concave profile. Additionally, as seen in FIGS. 11A and 11B, spool 320 includes two-pair of diametrically opposed lumens 326 formed around lumen 322 and extending entirely through spoon 320. Lumens 326 are configured to slidably receive articulation cables 240 therein.

As seen in FIGS. 1A, 1B and 12A-13E, ball joint 330 may be formed in a pair of halves 332a, 332b which are joined to one another define a lumen 332c therethrough. Ball joint 330 defines an arcuate distal surface 334 having a convex profile configured for operative engagement with the concave proximal surface of spool 320. Ball joint 330 further defines an outer annular flange 336 projecting radially outward therefrom. Flange 336 includes two-pair of diametrically opposed apertures 336a formed therearound. Ball joint 330 further includes a connecting hub 338 extending from a proximal surface thereof and defining an annular recess 338a formed therein.

Endoscopic device 100 includes a plurality of articulation cables 240 each having a first end anchored to flange 336 of ball joint 330 and a second end extending respective lumens 326 formed in spool 320, into lumen 316 of hub 310, through proximal outer tube 210, through respective lumens 232d, 234d formed in joints 232, 234, and anchored to distal support joint 238 of articulation assembly 230. In operation, as ball joint 330 is pivoted relative to spool 320, articulation cables 240 are either pulled or pushed to effectuate articulation of the distal end of endoscopic assembly 200.

As seen in FIGS. 1A, 1B and 14A-16D, collar 340 may be formed in a pair of halves 342a, 342b which are joined to one another define a lumen or cavity 342c therethrough. Collar 340 includes a distal flange 344 extending radially into lumen 342c and being configured for receipt in annular recess 338a of connecting hub 338 of ball joint 330. It is contemplated that annular recess 338a of connecting hub 338 of ball joint 330 and distal flange 344 of collar 340 may be dimensioned such that collar 340 is free to rotate relative to ball joint 330.

Figure 14A:
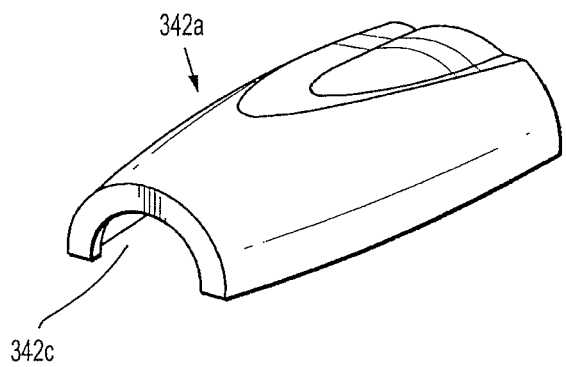
FIGS. 14A-14E are illustrations of a first half-section of a collar of the handle assembly of FIGS. 8A-8D.
Figure 14B:
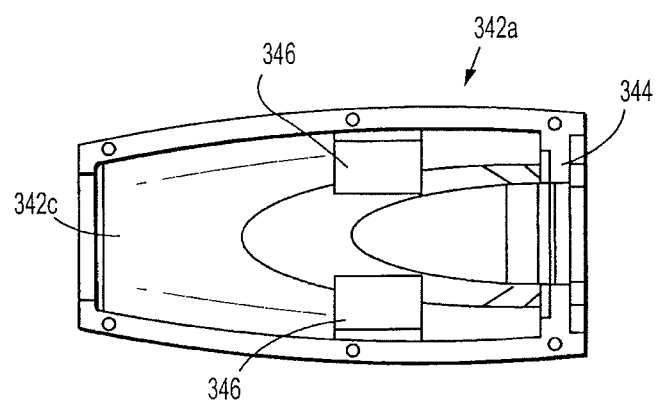
Figure 14C:
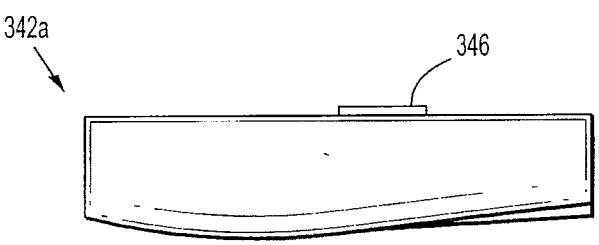
Figure 14E:
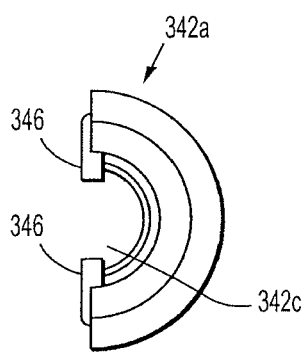
Figure 14D:
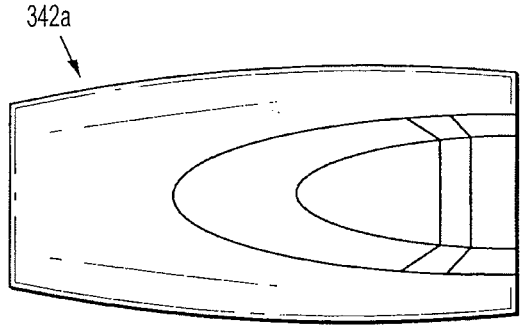
Figure 15A:
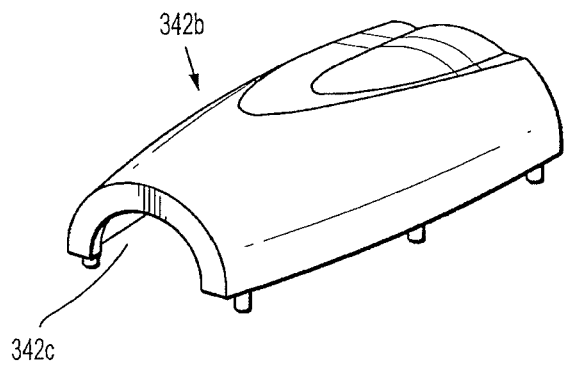
FIGS. 15A-15E are illustrations of a second half-section of the collar of the handle assembly of FIGS. 8A-8D.
Figure 15B:
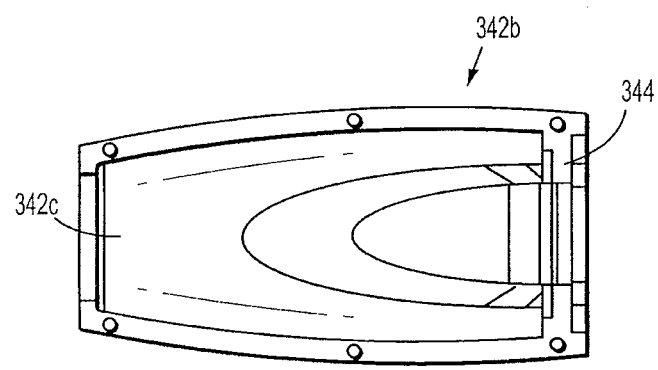
Figure 15C:
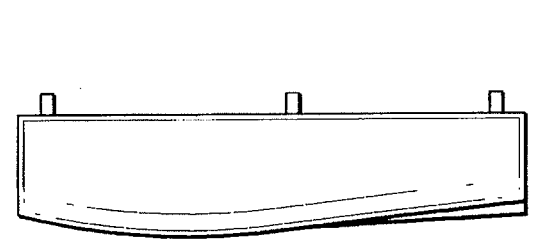
Figure 15E:
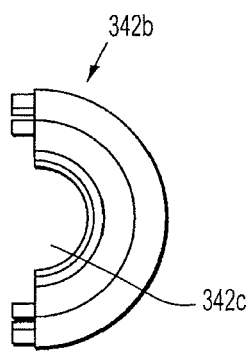
Figure 15D:
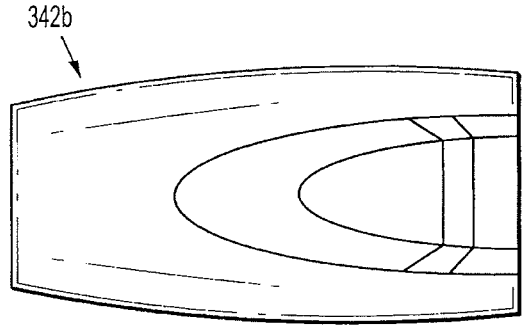
Figure 16A:
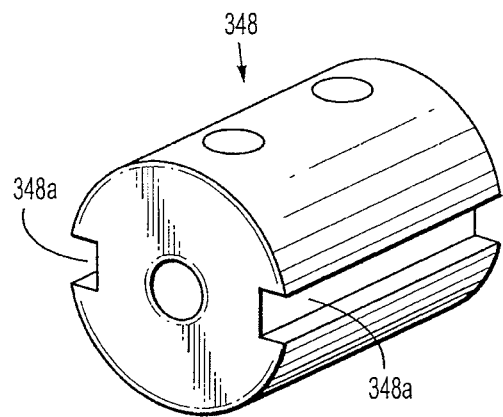
FIGS. 16A-16D are illustrations of a key member of the handle assembly of FIGS. 8A-8D.
Figure 16B:
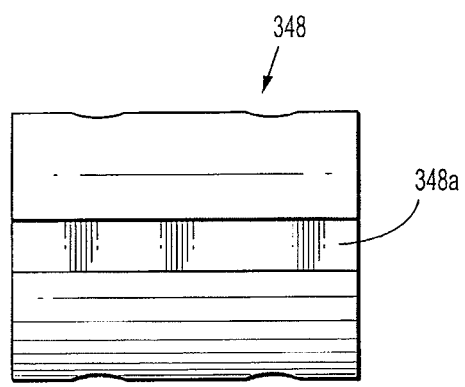
Figure 16D:
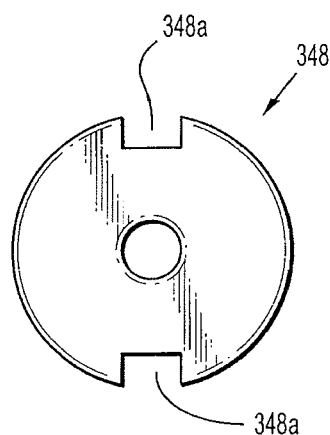
Figure 16C:
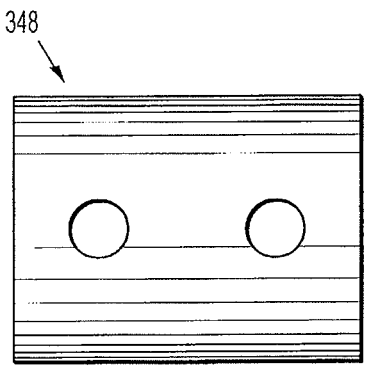

As seen in FIGS. 14C and 14E, collar 340 includes a pair of diametrically opposed guides 346 extending into lumen 342c. Guides 346 are configured and dimensioned for slidable receipt in races or slots 348a formed in a key member 348. Key member 348 is slidably disposed within lumen 342c of collar 342.

As seen in FIGS. 1A, 1B and 17A-17D, actuator 350 may include a loop 352 and a stem 354 extending therefrom. Loop 352 may be configured and dimensioned to receive a digit of the hand of the operator therein, such as, for example, the thumb. Actuator 350 is supported on a proximal end of collar 340 such that stem 354 extends into lumen 342c thereof.

As seen in FIGS. 18A-18D, handle assembly 300 includes a socket joint 356 having a first end 356a configured for connection to stem 354 of actuator 350, and a second end 356b defining a recess, hollow or socket 356c configured to receive a spherical head or ball (not shown) provided at a proximal end of the inner shaft (not shown). Socket joint 356 and the spherical head at the proximal end of the inner shaft cooperate with one another so as to enable rotation of socket joint 356, and in turn actuator 350, relative to the inner shaft. Additionally, socket joint 356 and the spherical head at the proximal end of the inner shaft cooperate with one another so as to enable axial translation of the inner shaft relative to collar 340, ball joint 330, spool 320, hub 310, and proximal and distal outer tubes 210, 220.

In operation, with reference to FIGS. 1A-3 and 8A-8D, as actuator 350 is translated relative to collar 340, as indicated by double-headed arrow "A", socket joint 356 transmits said translation to the inner shaft which in turn transmits said translation to the cam pin supported at the distal end thereof, to effectuate opening and/or closing of jaw assembly 260.

It is contemplated that handle assembly 300 may be provided with a locking or ratchet mechanism configured and adapted to function to maintain the position of actuator 350 as actuator 350 is depressed in a distal direction or towards hub 310. In this manner, jaw assembly 260 may be held in a fixed position, either partially closed or completely closed. It is further contemplated that the locking or ratchet mechanism will disengage, thereby allowing actuator 350 to return to an un-depressed position, following complete depression of actuator 350. It is also contemplated that actuator 350 may be biased to the un-depressed position by a suitable biasing element, such as, for example, a compression spring or the like.

Additionally, in operation, as collar 340 is rotated about the longitudinal axis, as indicated by arrows "B", relative to ball joint 330, spool 320 and actuator 350, collar 340 transmits rotation to key member 348 (see FIGS. 16A-16D). Since key member 348 is fixedly secured to the inner shaft, as collar 340 imparts rotation to key member 348, key member 348 imparts axial rotation to the inner shaft. As the inner shaft is rotated along the longitudinal axis, the inner shaft imparts rotation to the cam pin supported near the distal end thereof, which in turn imparts rotation of jaw assembly 260, as indicated by arrows "B" of FIG. 2A.

It is contemplated that handle assembly 300 may be provided with a locking or ratchet mechanism configured and adapted to function to maintain the position of collar 340 as collar 340 is rotated relative to ball joint 330, spool 320 and/or hub 310. In this manner, the angular orientation of jaw assembly 260 may be held in a fixed position. It is further contemplated that the locking or ratchet mechanism may be disengaged, thereby allowing collar 340 to freely rotate once again.

Also, in operation, as ball joint 330 is pivoted at the interface between arcuate distal surface 334 thereof and concave proximal surface of spool 320, in any radial direction relative to the longitudinal axis (i.e., omni-directionally or radially outward in 360° from the longitudinal axis), as exemplarily indicated by arrows "C", articulation cables 240 are pulled and/or pushed to effectuate omni-directional articulation of the distal end of endoscopic assembly 200 in any radial direction relative to the longitudinal axis.

It is contemplated that handle assembly 300 may be provided with a locking or ratchet mechanism configured and adapted to function to maintain the position of ball joint 330 as ball joint 330 is pivoted off-axis relative to spool 320 and/or hub 310. In this manner, the articulation of jaw assembly 260 may be held in a fixed position. It is further contemplated that the locking or ratchet mechanism may be disengaged, thereby allowing ball joint 330 to return to a centered position and jaw assembly 260 returned to a non-articulated position.

Turning now to FIGS. 19A-19F, a handle assembly 400 according to another embodiment of the disclosure is shown. Handle assembly 400 is substantially similar to handle assembly 300 and thus will only be discussed in detail herein to the extent necessary to identify differences in construction and/or operation.

Figure 19D:
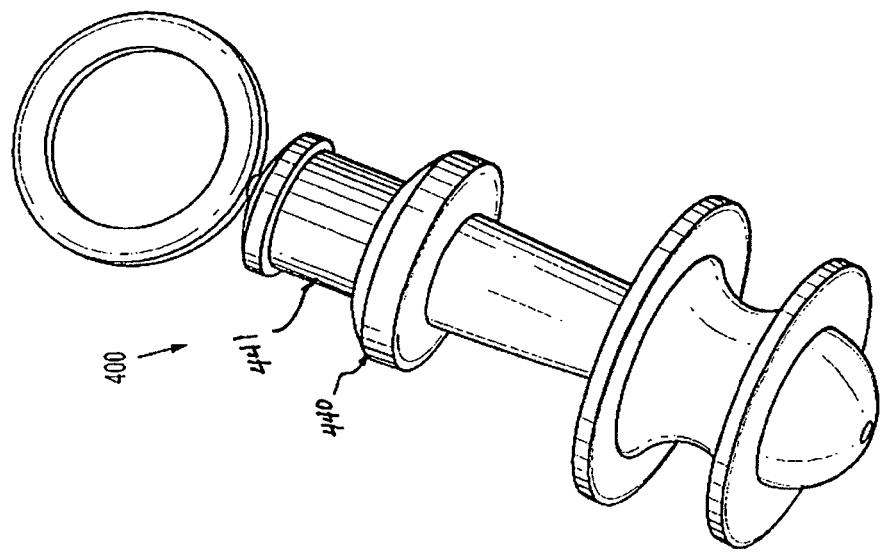
Figure 19C:
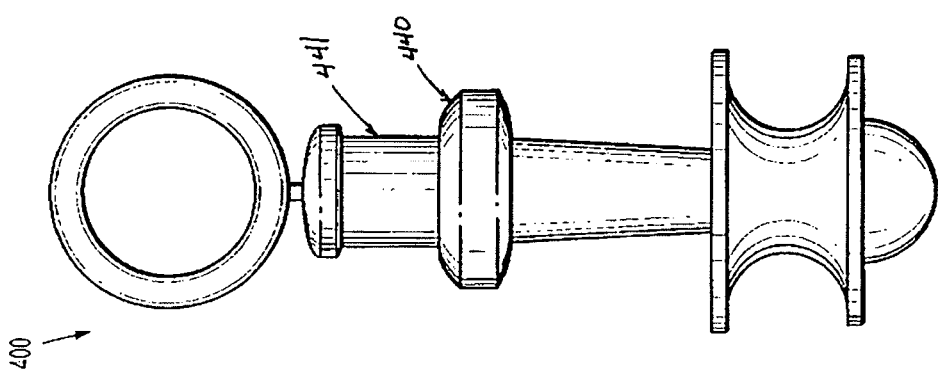
Figure 19B:
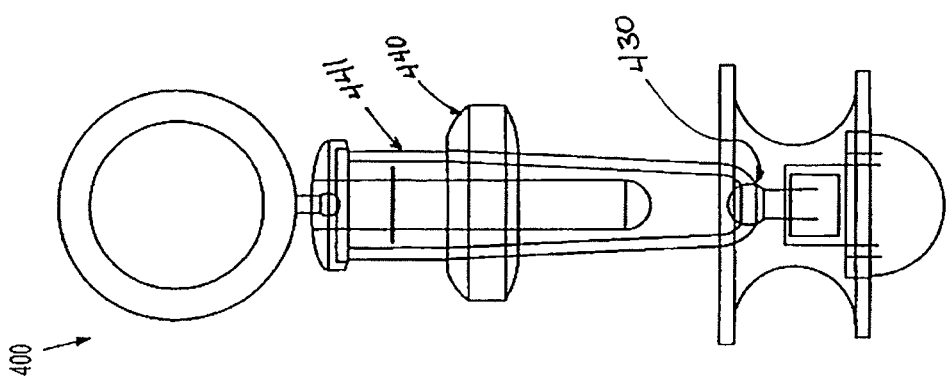
Figure 19F:
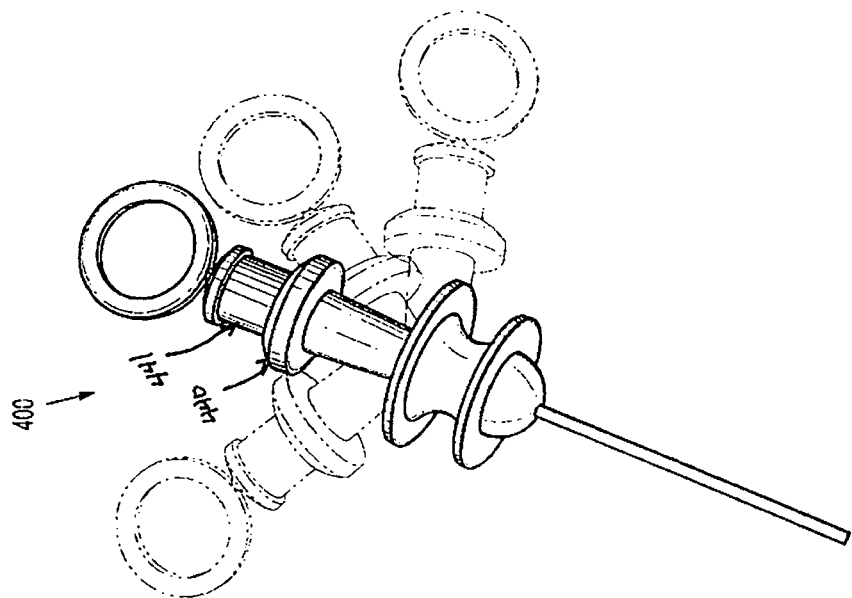
Figure 19E:
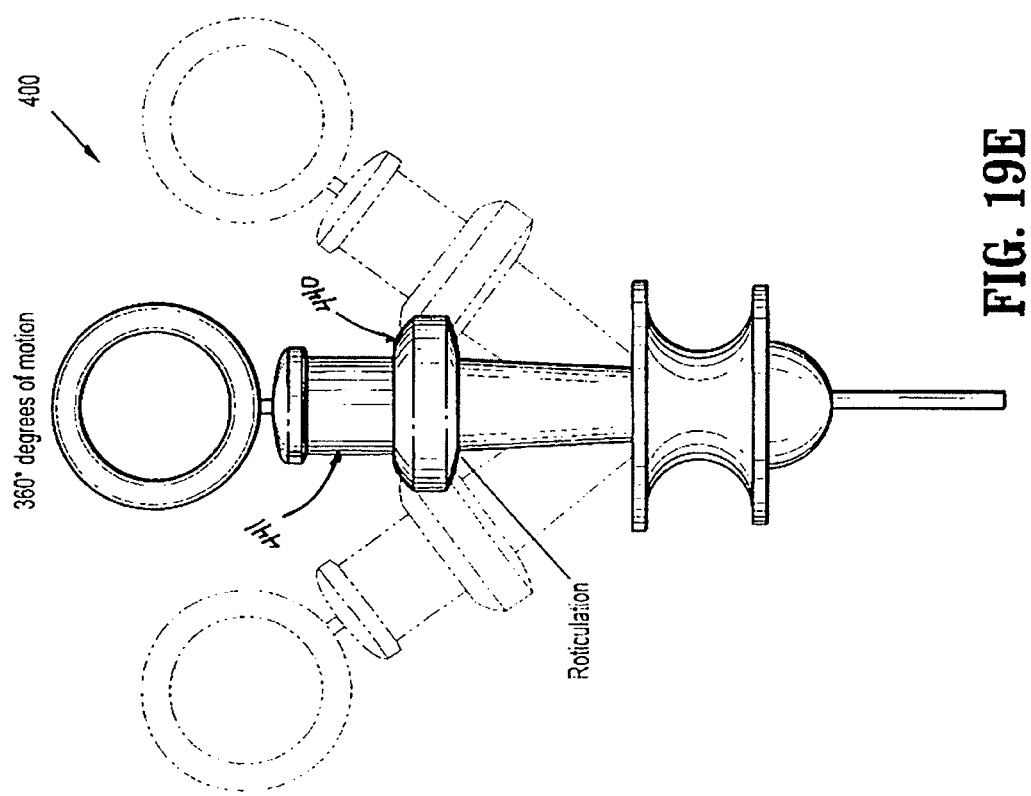

As seen in FIGS. 19A-19F, the handle assembly 400 includes a ring-like collar 440 configured to transmit rotation to the inner shaft (not shown). Additionally, the ring collar 440 is rotatably supported on a central housing 441, wherein the central housing 441 includes a rounded or arcuate distal end configured for pivotable engagement with the spool via a ball and socket connection 430, as seen in FIG. 19B. It is further contemplated that the actuation cables (not shown) may be anchored, at their proximal ends, to the central housing 441.

Figure 20B:
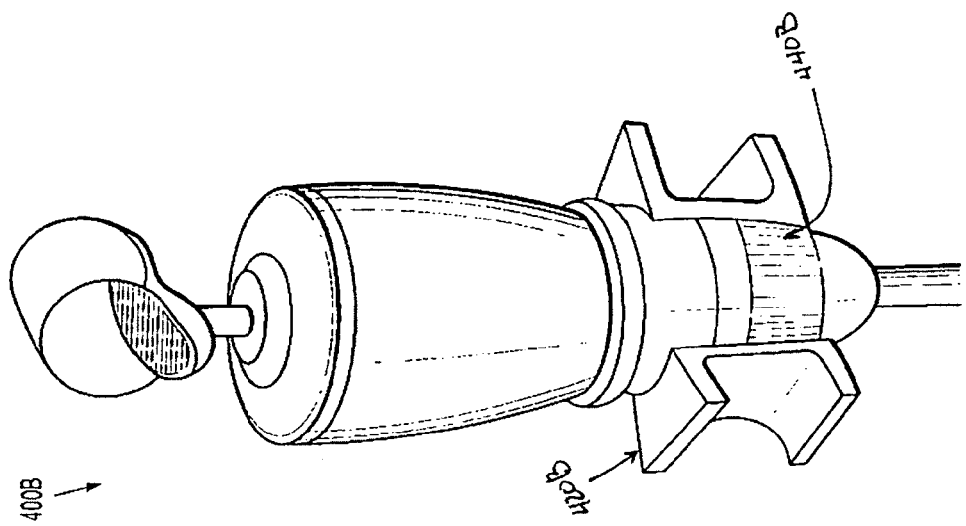
Figure 20A:
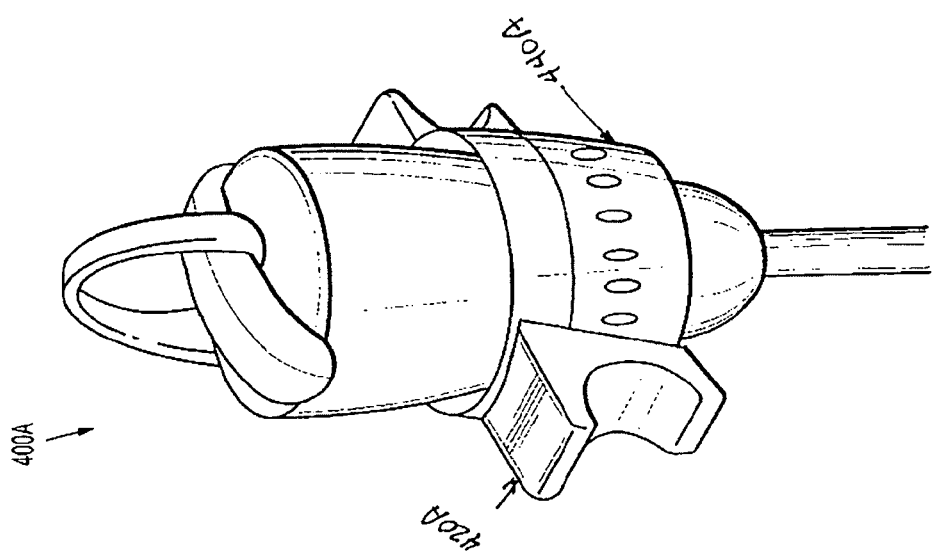

Turning now to FIGS. 20A-20J, various exemplary configurations of respective handle assemblies 400A-400J of the endoscopic device are illustrated. As seen in FIGS. 20A and 20B, respective spools 420A, 420B may extend partially around the handle assembly. It is further contemplated that respective ring collars 440A, 440B may be disposed beneath spools 420A, 420B. As seen in FIG. 20C, respective collar 440C may include tactile enhancing features, such as nubs 440C₁.

As seen in FIG. 20D, spool 420D may be formed in a proximal portion 420D₁ and a distal portion 420D₂.

Figure 20E:
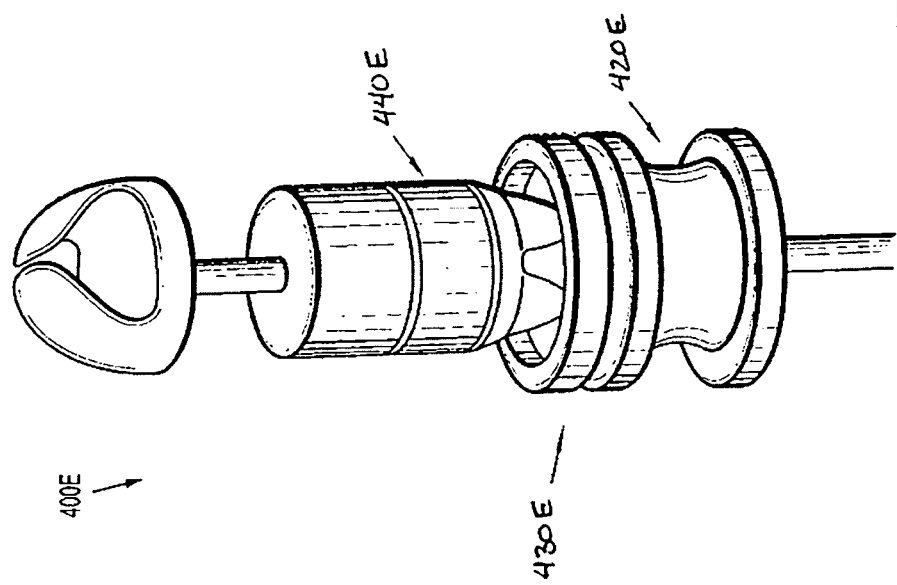
Figure 20G:
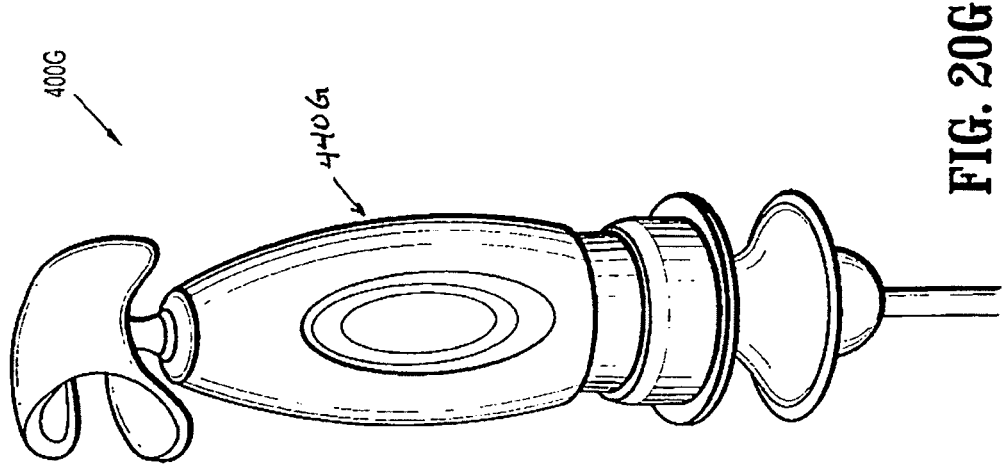

As seen in FIG. 20E, respective collar 440E, articulation assembly 430E, and spool 420E, may be shaped as cylinders and/or rings to provide a geometrically uniform appearance.

Figure 20F:
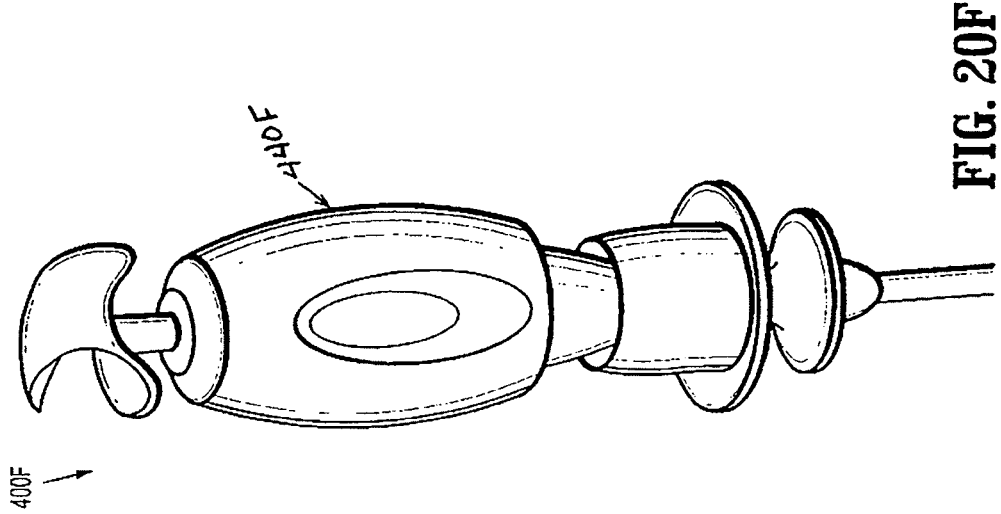

As seen in FIG. 20F, respective collar 440F may have a more ergonomic contour, and as seen in FIG. 440G, respective collar 440G may have an ergonomic contour having a lower profile as compared to collar 440F shown in FIG. 20F.

Figure 20H:
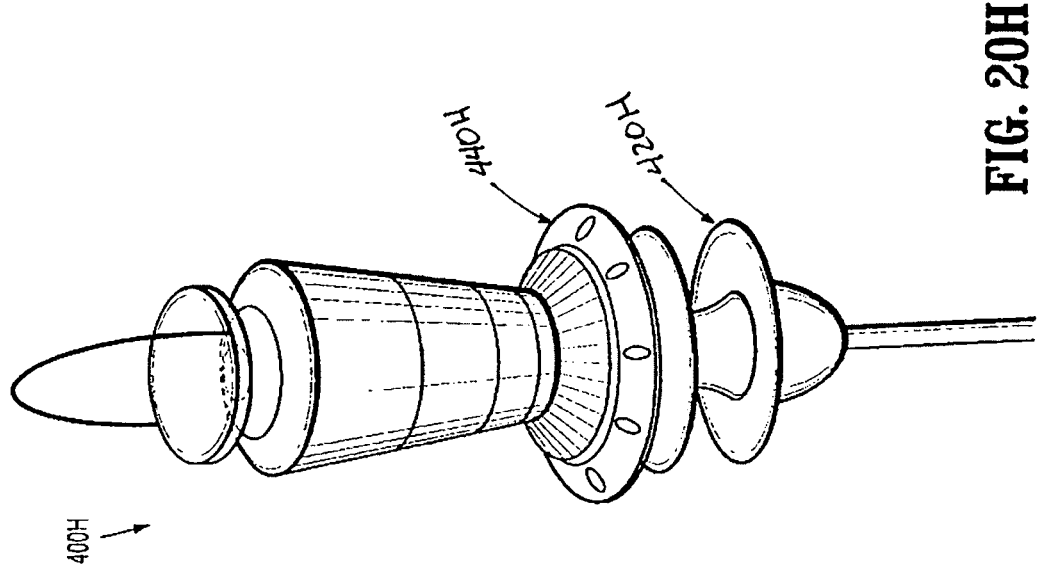

As seen in FIG. 20H, respective collar 440H may have a diameter that is greater than a diameter of respective spool 420H.

Figure 20I:
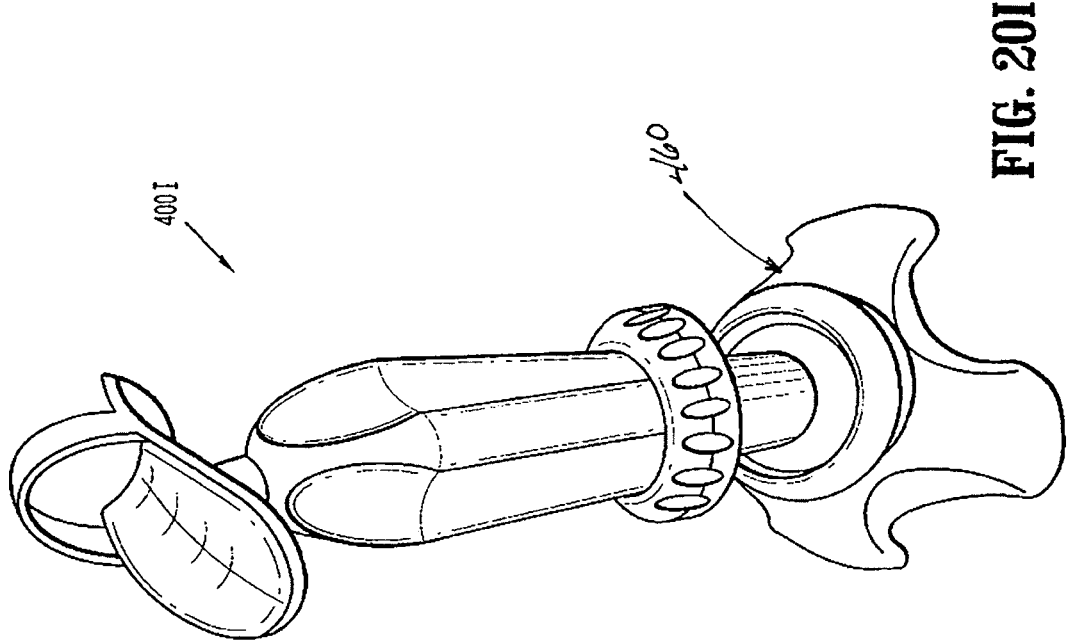

As seen in FIG. 20I, handle assemblies 400I may be used in cooperation with a guide member 460 for facilitating insertion of the endoscopic assembly (not shown) into the target surgical site.

Figure 20J:
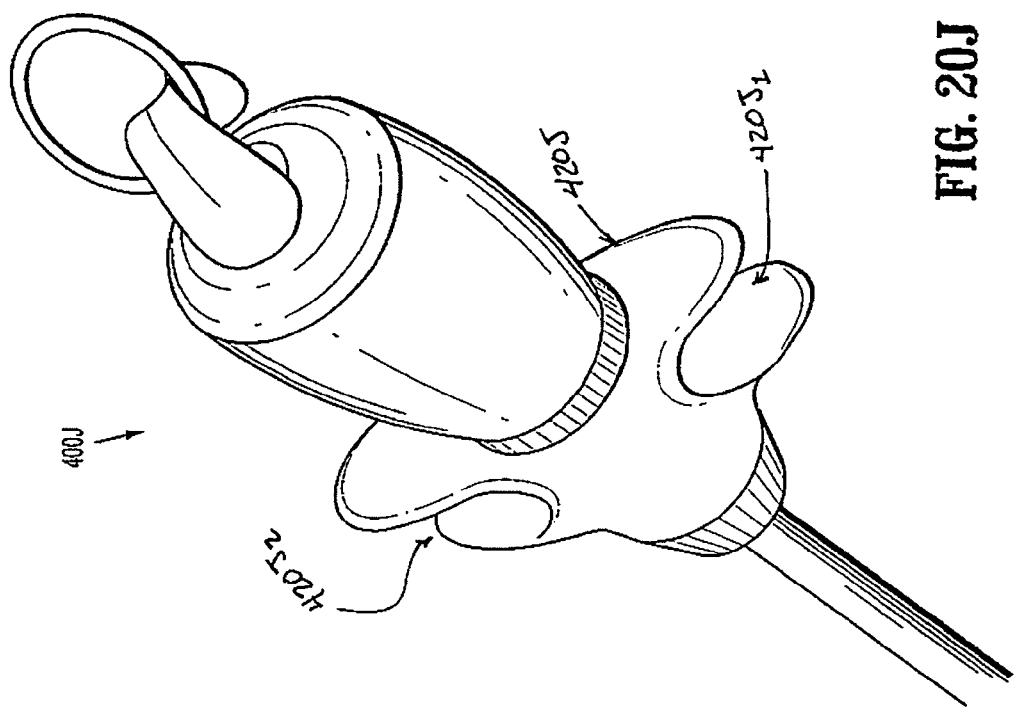

As seen in FIG. 20J, respective spool 420J may have a low profile and include only a pair of finger receiving areas 420J₁ and 420J₂ formed on opposed sides of handle assembly 400J.

Turning now to FIGS. 21A-21F, various exemplary configurations of respective actuators 350A-350F of the handle assembly of the endoscopic device are illustrated. As seen in FIG. 21A, respective actuator 350A may have a substantially C-shaped cross-sectional profile for facilitating insertion of a finger of a user therein. Actuator 350A may be rigidly connected to inner shaft 220. As seen in FIG. 21D, respective actuator 350D may be pivotally connected to the inner shaft 220. As seen in FIG. 21C, respective actuator 350C may include a pivotally connected strap 352C for surrounding the finger of the user, or as seen in FIG. 21E, respective actuator 350E may include an integrally formed strap 352E.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:
1. An endoscopic surgical device, comprising:
a handle assembly defining a longitudinal axis, the handle assembly including:
an articulation joint configured for off-axis tilting relative to the longitudinal axis;
a rotation collar configured for rotation about the longitudinal axis, the rotation collar having a keyed member disposed therein, wherein the rotation collar and the keyed member are connected to one another such that rotation of the rotation collar transmits rotation to the keyed member and such that the keyed member is axially movable relative to the rotation collar, the rotation collar disposed proximal of the articulation joint; and
an actuation member configured for axial translation along the longitudinal axis, the actuation member disposed proximal of the rotation collar;
a tube assembly operatively supported on and extending from the handle assembly, the tube assembly including:
a fixed outer tube; and
an inner shaft slidably and rotatably disposed in the outer tube, the inner shaft being connected to the keyed member and the actuation member, wherein rotation of the rotation collar results in rotation of the inner shaft and axial translation of the actuation member results in axial translation of the inner shaft;

an articulation assembly operatively supported on and extending from a distal end of the tube assembly, wherein the articulation assembly is configured for articulation in at least two axes transverse to the longitudinal axis, wherein the articulation assembly is controlled by the tilting of the articulation joint as a whole about a single pivot; and a tool assembly operatively supported on and extending from a distal end of the articulation assembly, wherein a distal end of the inner shaft is connected to the tool assembly such that axial translation of the inner shaft results in a first operation of the tool assembly and rotation of the inner shaft results in a second operation of the tool assembly.

2. The endoscopic surgical device according to claim 1, wherein the articulation assembly includes a plurality of joints operatively connected to one another, wherein the plurality of joints includes at least one knuckle permitting articulation in a first transverse direction relative to the longitudinal axis, and at least one knuckle permitting articulation in a second transverse direction relative to the longitudinal axis.

3. The endoscopic surgical device according to claim 2, wherein the at least one knuckle permitting articulation in the first transverse direction and the at least one knuckle permitting articulation in the second transverse direction are oriented substantially orthogonal to one another.

4. The endoscopic surgical device according to claim 1, wherein the articulation joint is a ball joint configured for radial articulation in any direction around the longitudinal axis, and the handle assembly includes a plurality of articulation cables each having a first end connected to the ball joint and each having a second end slidably extending through the tube assembly and the articulation assembly and being connected to the tool assembly, wherein tilting of the handle assembly about the ball joint, relative to the longitudinal axis, results in concomitant articulation of the tool assembly.

5. The endoscopic surgical device according to claim 4, wherein at least four evenly spaced articulation cables are provided around a central axis of the tube assembly.

6. The endoscopic surgical device according to claim 4, wherein as the handle is tilted off-axis, the ball joint exerts a force in a proximal direction on at least one of the plurality of articulation cables resulting in the concomitant articulation of the tool assembly.

7. The endoscopic surgical device according to claim 4, wherein the handle assembly includes a spool defining a central lumen therethrough and an off-set lumen for each of the plurality of articulation cables.

8. The endoscopic surgical device according to claim 7, wherein the spool defines a concave proximal surface configured for engagement with the ball joint.

9. The endoscopic surgical device according to claim 7, wherein the spool defines a concave annular outer surface.

10. The endoscopic surgical device according to claim 1, wherein the tool assembly includes a pair of juxtaposed jaws, wherein a distal end of the inner shaft is operatively connected to the jaws such that a reciprocation of inner shaft relative to the outer tube results in an opening and closing of the jaws, and a rotation of the inner shaft relative to the outer tube results in a rotation of the jaws.

11. The endoscopic surgical device according to claim 10, wherein each jaw defines a cam slot therein and wherein a cam pin is slidably disposed within each cam slot defined in the jaws, and wherein the cam pin is connected to the inner shaft such that translation of the inner shaft results in translation of the cam pin through the cam slots.

12. The endoscopic surgical device according to claim 1, wherein the keyed member defines at least one outer longitudinally extending groove and wherein the rotation collar includes at least one corresponding guide projecting into a respective groove of the keyed member, wherein rotation of the rotation collar imparts rotation to keyed member and the inner shaft and wherein the keyed member and the inner shaft are axially translatable relative to the rotation collar.

13. The endoscopic surgical device according to claim 1, wherein the inner shaft is bendable and is capable of transmitting rotational forces and axial forces.

14. An endoscopic surgical device, comprising:

a handle assembly defining a longitudinal axis, the handle assembly including:
   an articulation joint configured for omni-directional off-axis tilting relative to the longitudinal axis;
   a rotation collar configured for rotation about the longitudinal axis, the rotation collar disposed proximal of the articulation joint; and
   an actuation member configured for axial translation along the longitudinal axis, the actuation member disposed proximal of the rotation collar;

a tube assembly operatively supported on and extending from the handle assembly, the tube assembly including:
   a fixed outer tube; and
   an inner shaft slidably and rotatably disposed in the outer tube, wherein the inner shaft is connected to the rotation collar and the actuation member such that rotation of the rotation collar results in rotation of the inner shaft and axial translation of the actuation member results in axial translation of the inner shaft;

an articulation assembly operatively supported on and extending from a distal end of the tube assembly, wherein the articulation assembly is configured for omni-directional articulation concomitant with the omni-directional tilting of the articulation joint as a whole about a single pivot; and a tool assembly operatively supported on and extending from a distal end of the articulation assembly, wherein a distal end of the inner shaft is connected to the tool assembly such that axial translation of the inner shaft results in a first operation of the tool assembly and rotation of the inner shaft results in a second operation of the tool assembly.

15. The endoscopic surgical device according to claim 14, wherein the rotation collar includes a keyed member disposed therein, wherein the rotation collar and the keyed member are connected to one another such that rotation of the rotation collar transmits rotation to the keyed member and such that the keyed member is axially movable relative to the rotation collar.

16. The endoscopic surgical device according to claim 15, wherein the inner shaft is connected to the keyed member and the actuation member.

17. The endoscopic surgical device according to claim 15, wherein the keyed member defines at least one outer longitudinally extending groove and wherein the rotation collar includes at least one corresponding guide projecting into a respective groove of the keyed member, wherein rotation of the rotation collar imparts rotation to keyed member and the inner shaft and wherein the keyed member and the inner shaft are axially translatable relative to the rotation collar.

18. The endoscopic surgical device according to claim 14, wherein the articulation assembly includes a plurality of joints operatively connected to one another, wherein the plurality of joints includes at least one knuckle permitting articulation in a first transverse direction relative to the longitudinal axis, and at least one knuckle permitting articulation in a second transverse direction relative to the longitudinal axis.

19. The endoscopic surgical device according to claim 18, wherein the at least one knuckle permitting articulation in the first transverse direction and the at least one knuckle permitting articulation in the second transverse direction are oriented substantially orthogonal to one another.

20. The endoscopic surgical device according to claim 14, wherein the articulation joint is a ball joint, and the handle assembly includes a plurality of articulation cables each having a first end connected to the ball joint and each having a second end slidably extending through the tube assembly and the articulation assembly and being connected to the tool assembly, wherein tilting of the handle assembly in any direction about the ball joint, relative to the longitudinal axis, results in concomitant articulation of the tool assembly.

21. The endoscopic surgical device according to claim 20, wherein at least four evenly spaced articulation cables are provided around a central axis of the tube assembly.

22. The endoscopic surgical device according to claim 21, wherein as the handle is tilted off-axis, the ball joint exerts a force in a proximal direction on at least one of the plurality of articulation cables resulting in the concomitant articulation of the tool assembly.

23. The endoscopic surgical device according to claim 20, wherein the handle assembly includes a spool defining a central lumen therethrough and an off-set lumen for each of the plurality of articulation cables.

24. The endoscopic surgical device according to claim 23, wherein the spool defines a concave proximal surface configured for engagement with the ball joint.

25. The endoscopic surgical device according to claim 23, wherein the spool defines a concave annular outer surface.

26. The endoscopic surgical device according to claim 14, wherein the tool assembly includes a pair of juxtaposed jaws, wherein the distal end of the inner shaft is operatively connected to the jaws such that a reciprocation of inner shaft relative to the outer tube results in an opening and closing of the jaws, and a rotation of the inner shaft relative to the outer tube results in a rotation of the jaws.

27. The endoscopic surgical device according to claim 26, wherein each jaw defines a cam slot therein and wherein a cam pin is slidably disposed within each cam slot defined in the jaws, and wherein the cam pin is connected to the inner shaft such that translation of the inner shaft results in translation of the cam pin through the cam slots.

28. The endoscopic surgical device according to claim 14, wherein the inner shaft is bendable and is capable of transmitting rotational forces and axial forces.

* * * * *